United States Patent
Semenov et al.

(10) Patent No.: US 11,360,294 B2
(45) Date of Patent: Jun. 14, 2022

(54) OPTICAL SENSOR

(71) Applicant: Samsung Electronics Co., Ltd., Suwon-si (KR)

(72) Inventors: Vladimir Mikhailovich Semenov, Moscow (RU); Artem Andreevich Dolgoborodov, Moscow (RU); Anastasiia Sergeevna Suvorina, Moscow (RU); Gennady Dmitrievich Mamykin, Moscow (RU); Dmitrii Igorevich Chernakov, Moscow (RU); Vladislav Valerievich Lychagov, Moscow (RU)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/953,994

(22) Filed: Nov. 20, 2020

(65) Prior Publication Data
US 2021/0356724 A1 Nov. 18, 2021

(30) Foreign Application Priority Data

May 15, 2020 (RU) .......................... RU2020115881
Sep. 25, 2020 (KR) ........................ 10-2020-0125145

(51) Int. Cl.
*G02B 17/08* (2006.01)
*G02B 27/30* (2006.01)
(Continued)

(52) U.S. Cl.
CPC ............ *G02B 17/0876* (2013.01); *G01J 9/02* (2013.01); *G01N 15/0205* (2013.01); *G02B 5/10* (2013.01);
(Continued)

(58) Field of Classification Search
CPC .......... G01B 9/02051; G01N 15/0205; G01N 2015/0233; G02B 27/10; G02B 27/1086;
(Continued)

(56) References Cited

U.S. PATENT DOCUMENTS 4,523,846 A * 6/1985 Breckinridge ........ G01J 3/4531
356/456
4,671,613 A 6/1987 Buhrer
(Continued)

FOREIGN PATENT DOCUMENTS

JP 2005-003572 A 1/2005
JP 3702440 B2 10/2005
(Continued)

OTHER PUBLICATIONS

English translation of WO 00/58960. Obtained from Espacenet on Sep. 28, 2021. (Year: 2021).*
(Continued)

*Primary Examiner* — Michael A Lyons
(74) *Attorney, Agent, or Firm* — Jefferson IP Law, LLP

(57) ABSTRACT

The disclosure relates to multifunctional sensors for mobile applications, namely to a miniature optical sensor for remote micro- and macro-object detection and characterization. The disclosure makes it possible to reduce the size of the sensor, this provides for surface mount of the sensor in any microcircuit of a mobile device. The sensor is multifunctional, low-power, vibration-resistant. The sensor comprises at least one pair consisting of a radiation source and a corresponding radiation receiver, an optical circuit including a collimating element, a first optical element, a second optical element. The first optical element and the second optical element are interconnected by a common surface, the common surface being a semitransparent surface. The sensor may be used
(Continued)

simultaneously as a microphone, a dust sensor, a lidar, and a photoplethysmogram (PPG) sensor.

22 Claims, 20 Drawing Sheets

(51) Int. Cl.
*H01S 5/02255* (2021.01)
*G02B 5/10* (2006.01)
*G01N 15/02* (2006.01)
*G01J 9/02* (2006.01)
*H01S 5/00* (2006.01)
*H04R 23/00* (2006.01)
*G01S 7/481* (2006.01)

(52) U.S. Cl.
CPC ......... *G02B 17/0868* (2013.01); *G02B 27/30* (2013.01); *H01S 5/0064* (2013.01); *H01S 5/02255* (2021.01); *G01S 7/4812* (2013.01); *H04R 23/008* (2013.01)

(58) Field of Classification Search
CPC ... G02B 27/1093; G02B 27/14; G01J 3/4532; G01J 2003/4534
See application file for complete search history.

(56) References Cited

U.S. PATENT DOCUMENTS

| | | | | |
|---|---|---|---|---|
| 5,148,317 | A * | 9/1992 | Foresi | G02B 5/1876 359/566 |
| 7,372,577 | B1 * | 5/2008 | Sullivan | G01B 9/02051 356/451 |
| 9,658,219 | B2 | 5/2017 | Verschuren et al. | |
| 9,664,909 | B1 | 5/2017 | Whiteside et al. | |
| 10,225,442 | B2 | 3/2019 | Tseng et al. | |
| 10,386,283 | B2 | 8/2019 | Trainer | |
| 11,054,309 | B2 | 7/2021 | Suzuki et al. | |
| 11,067,380 | B2 | 7/2021 | Suzuki et al. | |
| 2006/0244971 | A1 * | 11/2006 | Belt | G01B 9/02051 356/487 |
| 2008/0049190 | A1 | 2/2008 | Destain et al. | |
| 2014/0226158 | A1 | 8/2014 | Trainer | |
| 2018/0209892 | A1 | 7/2018 | Van Der Lee et al. | |
| 2018/0275396 | A1 | 9/2018 | Schowengerdt et al. | |
| 2019/0086316 | A1 | 3/2019 | Rice et al. | |
| 2020/0124472 | A1 | 4/2020 | Suzuki et al. | |
| 2020/0124473 | A1 | 4/2020 | Suzuki et al. | |
| 2020/0124479 | A1 | 4/2020 | Suzuki et al. | |
| 2020/0124480 | A1 | 4/2020 | Suzuki et al. | |
| 2020/0142155 | A1 | 5/2020 | Suzuki et al. | |
| 2021/0132364 | A1 | 5/2021 | Suzuki et al. | |
| 2021/0148690 | A1 | 5/2021 | Suzuki et al. | |

FOREIGN PATENT DOCUMENTS

| | | | |
|---|---|---|---|
| JP | 2015-072137 A | 4/2015 | |
| JP | 6514841 B1 | 5/2019 | |
| JP | 2020-020761 A | 2/2020 | |
| KR | 10-2001-0110477 A | 12/2001 | |
| KR | 10-2019-0000995 A | 1/2019 | |
| SU | 558579 A1 | 12/1977 | |
| WO | 2007/016199 A2 | 2/2007 | |
| WO | 2019/115278 A1 | 6/2019 | |
| WO | WO-2019129497 A1 * | 7/2019 | ............ G01J 3/4532 |

OTHER PUBLICATIONS

International Search Report and written opinion dated May 20, 2021, issued in International Application No. PCT/KR2021/000993.

Russian Patent Office Search Report dated Sep. 23, 2020, in Russian Application No. 2020115881.

Russian Patent Office Decision on Grant dated Oct. 1, 2020, issued in Russian Application No. 2020115881.

\* cited by examiner

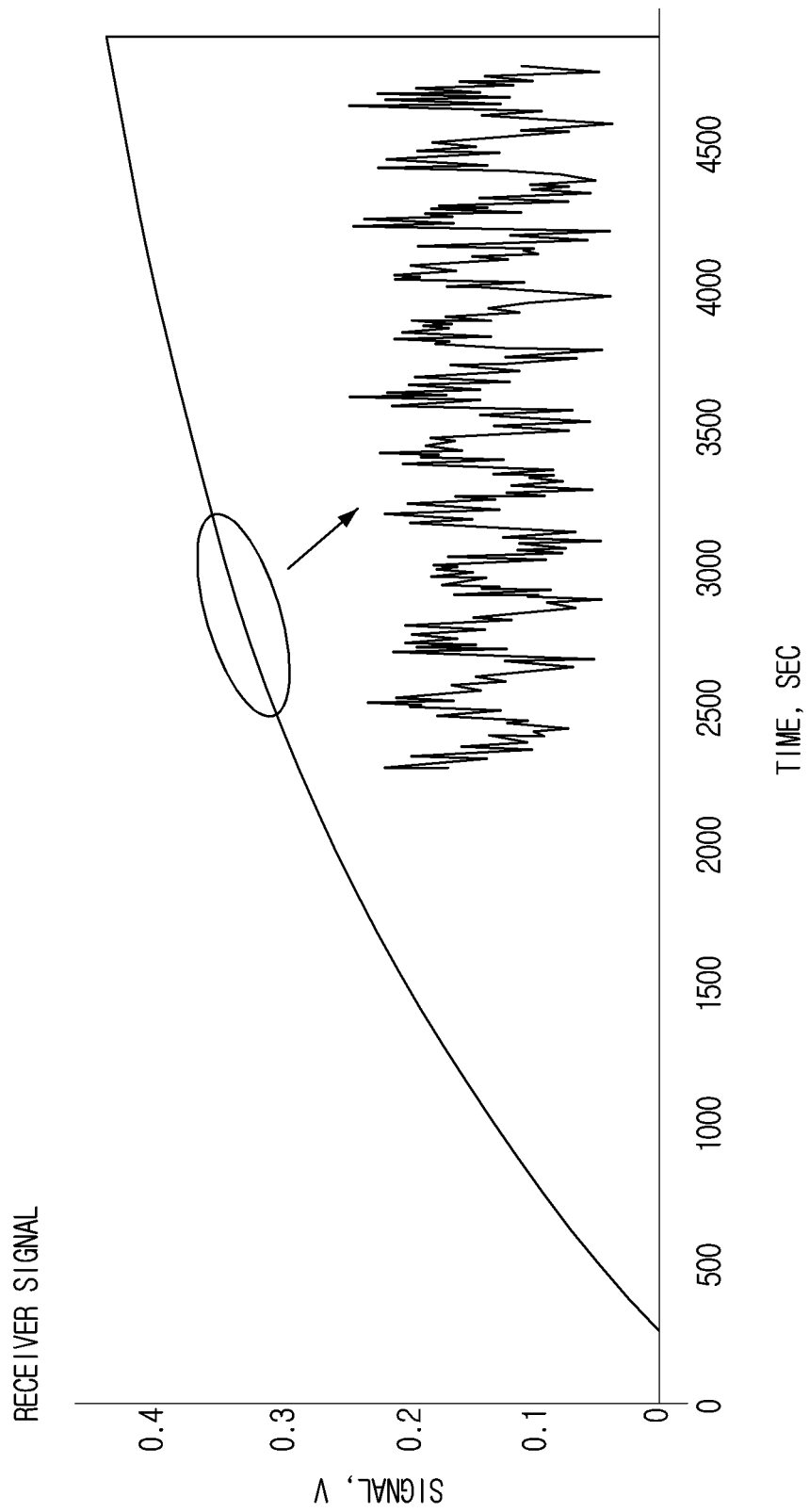

OPTICAL SENSOR

CROSS-REFERENCE TO RELATED APPLICATION(S)

This application is based on and claims priority under 35 U.S.C. § 119(a) of a Russian patent application number 2020115881, filed on May 15, 2020, in the Russian Federation Federal Service for Intellectual Property Office, and of a Korean patent application number 10-2020-0124145, filed on Sep. 25, 2020, in the Korean Intellectual Property Office, the disclosure of each of which is incorporated by reference herein in their entireties.

BACKGROUND

1. Field

The disclosure relates to multifunctional sensors for mobile applications, namely to a miniature optical sensor for remote micro- and macro-object detection and characterization.

2. Description of the Related Art

The environmental concerns of large cities are driving a growing user demand for fine dust and gas sensors that users may use as a function of their mobile devices. It should be noted that air quality is one of the most important factors affecting human health. Particles which are larger than 10 microns that enter the body with respiration are mainly retained in the upper respiratory tract, while particles which are smaller than 5-10 microns penetrate into the lungs. Particles up to 2.5 microns in size are especially dangerous to health, because such particles may participate in the gas exchange of the pulmonary alveoli and are carcinogenic, and particles less than 0.1 microns (100 nm) in size penetrate through the cell membranes and reach other organs of the body through the bloodstream. In many countries, particulate matter (PM) concentrations (PM2.5 for <2.5 μm particles and PM10 for <10 μm particles) are included in the air quality index. The PM2.5 and PM10 concentration may vary significantly over time and location, so it is important for the user to measure the concentration of dust in certain places of his stay and to be aware of the environmental situation in his vicinity at any time.

However, today, sensors used in dust detection devices such as weather stations, air cleaners, and air conditioners are bulky, expensive, difficult to handle, and suitable for use only by trained technicians. In common consumer electronics with a dust removal function, such as air cleaners and air conditioners, optical light emitting diode (LED) sensors measuring 5 cm×3 cm×2 cm are usually implemented, and it is obvious that sensors of this size may not be used in mobile devices.

Many miniature sensors have been developed that perform various functions that may be used in smartphones, smart watches and other mobile devices. Thanks to such miniature sensors, a user may, for example, measure the pulse, recognize gestures, use three-dimensional cameras and video cameras, use an accelerometer and gyroscope which allow determining the position in space and movement characteristics, take panoramic photos, etc. Increasing the functionality of smart devices by embedding new sensors has obvious limitations in that more sensors require more space and increase the energy consumption, heat load, and cost of mobile devices.

A solution to these problems is to develop a universal sensor that combines many functions. It is known that interferometry makes it possible to measure distances, speeds, vibrations, movements, etc., and has sufficient sensitivity for fixing micro-objects. However, most interferometer-based sensors are not suitable for surface mount because most interferometer designs are too bulky and not very robust. In addition, the interferometric approach requires the use of many separate optical elements (prisms, beam splitters, lenses, mirrors, polarizers, etc.) and complex alignment procedures, the location of the radiation source and the radiation receiver in different planes, which reduces reliability, increases production costs, limits the possibilities of surface mounting and miniaturization. Obviously, such cumbersome arrangements are not suitable for use in mobile devices. Mobile devices require a miniature, fairly flat sensor that may be mounted to one board without increasing the overall dimensions of the mobile device.

A Michelson interferometer may be used for spectral analysis of a sample. This is used as a converting spectroscopic interferometer or a device for measuring the distance of movement. Drawbacks of this solution include the impossibility of using it in mobile devices, the impossibility of combining in the known device such functions as measuring the concentration of particles, measuring the distance to macro objects, measuring the speed of macro objects, etc.

Various modifications of a monolithic beam splitter with an integrated focusing lens are also known. The drawbacks of this solution include the impossibility of surface mounting, that is, the problem of the planar arrangement of the laser and the detector is not solved, as well as the impossibility of combining in the known device such functions as measuring the concentration of particles, measuring the distance to macro-objects, measuring the speed of macro-objects.

Another method and apparatus for determining particle characteristics include an illuminating source and a light detector for detecting light scattered from one or more particles, a reflector for reflecting light from the illuminating source to the detector, wherein light reflected from the reflector is combined with light scattered from one or more particles to produce an interference signal. Drawbacks of this solution include the impossibility of combining the above-mentioned functions in the known device, and also the impossibility of using it in mobile devices, the impossibility of combining in the known device such functions as measuring the concentration of particles, measuring the distance to macro objects, measuring the speed of macro objects, etc. In addition, a study of this solution is carried out in a chamber, that is, for the study, air is pumped into the chamber from free space.

Most of the related art devices and sensors are too bulky and cannot be built into small mobile devices such as smart-phones, smart watches, etc. In addition, related art sensors are not very informative and do not have the ability to perform several measurements at once.

In view of the above, a flat miniature sensor is needed that may be used in mobile devices. One miniature sensor should be a multifunctional device that combines, in addition to measuring dust concentration, such functions as measuring the concentration of particles, measuring the distance to macro objects, and measuring the speed of macro objects.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an optical sensor which includes at least one pair consisting of a radiation source and a corresponding radiation receiver, an optical circuit including a collimating element, a first optical element, a second optical element, wherein the collimating element is configured to collimate radiation from the radiation source, the first optical element and the second optical element are interconnected by a common surface, the first optical element comprising an input surface for receiving radiation, a reflective surface of the first optical element for reflecting radiation that has passed through the input surface and directing the reflected radiation to the common surface, a working surface for emitting the radiation reflected from the common surface and receiving the radiation reflected from an object or scattered by an object, the second optical element comprising a reflective surface of the second optical element for reflecting the radiation that has passed through the common surface, an output surface for emitting the radiation and the radiation reflected from the object or scattered by the object to the radiation receiver corresponding to the radiation source.

Moreover, wherein the common surface may be configured to separate radiation from the reflective surface of the first optical element into reference radiation and working radiation, the working surface of the first optical element may be configured to emit the working radiation reflected from the common surface, the output surface of the second optical element may be configured to reflecting the reference radiation that has passed through the common surface, and the output surface of the second optical element may be configured to emit the reference radiation to the radiation receiver corresponding to the radiation source.

Moreover, all radiation sources and radiation receivers may be located in the same plane.

Moreover, the collimating element may be integrated with the radiation source. Moreover, the collimating element may be integrated with the first optical element. The working surface may be configured to focus the working radiation. The working surface may be made in the form of a spherical lens or an aspherical lens. Moreover, the working surface may be flat. The at least one radiation source may be a vertical emitting laser (VCSEL). The output surface may be configured to focus the emitted radiation. The collimating element may be integrated with the reflective surface of the first optical element, and is made in the form of an off-axis parabolic mirror. The collimating element may be in the form of a diffractive optical element (DOE) or a holographic optical element (HOE). The working surface may be coated with the DOE or the HOE. The collimating element may be in the form of the DOE or the HOE applied to the input surface of the first optical element. Moreover, each of the at least one pair, consisting of the radiation source and the corresponding radiation receiver, operate at a predetermined wavelength. The multifunctional optical sensor may further comprise a quarter-wave plate embedded in the input surface of the first optical element, wherein at least one radiation source is a laser with a fixed polarization.

Additional aspects will be set forth in part in the description which follows and, in part, will be apparent from the description, or may be learned by practice of the presented embodiments.

In accordance with an aspect of the disclosure, an optical sensor is provided. The optical sensor includes at least one pair consisting of a radiation source and a corresponding radiation receiver, an optical circuit including a collimating element, a first optical element, a second optical element, wherein: the collimating element is configured to collimate radiation from the radiation source, the first optical element and the second optical element are interconnected by a common surface, the common surface being a semitransparent surface, the first optical element comprising an input/output surface for inputting radiation from the radiation source and directing to the semitransparent surface, wherein, the semitransparent surface is configured to divide the radiation inputted through the input/output surface into reference radiation and working radiation, emit reference radiation and the radiation reflected from an object or scattered by an object to the radiation receiver, emitting the reference radiation and the radiation reflected from the object or scattered by the object to the radiation receiver, a reflective surface of the first optical element for directing the reference radiation reflected from the semitransparent surface and the radiation reflected from the object or scattered by the object to the input/output surface for emitting from the optical circuit to the radiation receiver, the second optical element comprising a working surface for emitting the working radiation that has passed through the semitransparent surface and receiving the radiation reflected from the object or scattered by the object, a reflective surface for directing radiation reflected from the object or scattered by the object through the semitransparent surface to the reflective surface of the first optical element, wherein, all radiation sources and radiation receivers are located in the same plane. Moreover, the collimating element may be integrated with the radiation source. The collimating element may be integrated with the first optical element. The working surface may be configured to focus the working radiation. The working surface is made in the form of a spherical lens or an aspherical lens. The working surface may be flat. The at least one radiation source is a VCSEL. The input-output surface may be configured to focus the emitted radiation. The collimating element may be in the form of a DOE or an HOE. The working surface may be coated with the DOE or the HOE. The collimating element may be in the form of the DOE or the HOE applied to the input-output surface of the first optical element. Moreover, each of at the least one pair, consisting of the radiation source and the corresponding radiation receiver, operates at a predetermined wavelength. The collimating element may be integrated with the reflective surface of the first optical element, and is made in the form of an off-axis parabolic mirror.

In accordance with another aspect of the disclosure, the use of the above-described optical sensor as a microphone, dust sensor, light detection and ranging (lidar), photoplethysmogram (PPG) sensor is provided.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features and advantages of certain embodiments of the disclosure will be more apparent from the following description taken in conjunction with the accompanying drawings, in which:

FIG. 11A illustrates a graph of voltage of the signal reflected from the macro object versus time according to an embodiment of the disclosure;

The same reference numerals are used to represent the same elements throughout the drawings.

DETAILED DESCRIPTION

Figure 1:
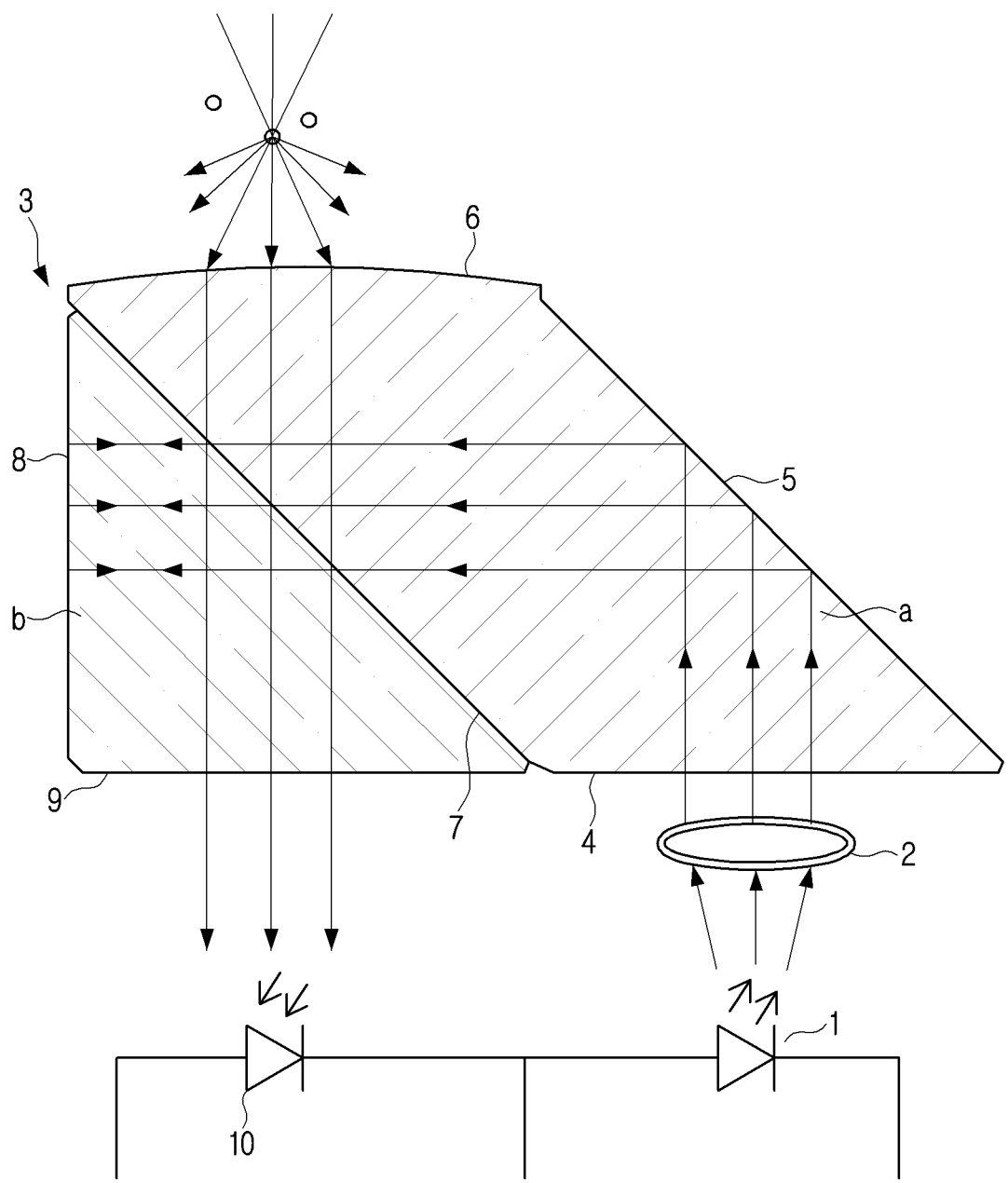
FIG. 1 shows an embodiment of a multifunctional miniature sensor according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terms used in this disclosure will be briefly described, and the disclosure will be described in greater detail.

General terms that are currently widely used were selected as terms used in embodiments of the disclosure in consideration of functions in the disclosure, but may be changed depending on the intention of those skilled in the art or a judicial precedent, the emergence of a new technique, and the like. In addition, in a specific case, terms may be arbitrarily chosen. In this case, the meaning of such terms will be apparent from a corresponding description portion of the disclosure. Therefore, the terms used in embodiments of the disclosure should be defined based on the meaning of the terms and the contents throughout the disclosure rather than simple names of the terms.

In this disclosure, the expressions "have," "may have," "include," or "may include" or the like indicate the presence of a corresponding feature (for example: components such as numbers, functions, operations, or parts) and does not exclude the presence of additional feature.

The expression "At least one of A or/and B" should be understood to represent "A" or "B" or any one of "A and B."

As used herein, the terms "first," "second," or the like may denote various components, regardless of order or importance, and may be used to distinguish one component from another, and does not limit the components.

In addition, the description in the disclosure that one element (e.g., a first element) is "(operatively or communicatively) coupled with/to" or "connected to" another element (e.g., a second element) should be interpreted to include both the case in which the one element is directly coupled to the another element, and the case in which the one element is coupled to the another element through still another element (e.g., a third element).

A singular expression includes a plural expression, unless otherwise specified. It is to be understood that the terms such as "comprise" or "consist of" are used herein to designate a presence of a characteristic, number, step, operation, element, component, or a combination thereof, and not to preclude a presence or a possibility of adding one or more of other characteristics, numbers, steps, operations, elements, components or a combination thereof.

The term such as "module," "unit," "part," and so on is used to refer to an element that performs at least one function or operation, and such element may be implemented as hardware or software, or a combination of hardware and software. Further, except for when each of a plurality of "modules," "units," "parts," and the like needs to be realized in an individual hardware, the components may be integrated in at least one module or chip and be realized in at least one processor (not shown).

Hereinafter, embodiments of the disclosure will be described in greater detail with reference to the accompanying drawings.

A multifunctional miniature chip-sized sensor for micro- and macro-object detection and characterization is provided. In the disclosure, an object means any micro-objects, such as, for example, fine dust particles, red blood cells, or macro-sized objects located at some distance from the sensor.

The multifunctional sensor provides the following advantages:

a miniature size, which allows it to be embedded in a microchip of a mobile device without changing the modification of the mobile device;

low-power consumption;

vibration-resistance;

eye safe, since the power of the used radiation source does not exceed the maximum permissible values according to GOST IEC 60825-1-2013 Standard; and multi-functionality, that is, it may operate in different modes, including the functions of a dust sensor, a macro object proximity sensor, a sensor for measuring vibration/distance to a macro object, that is, micro-movement of a micro-object/movement of a macro-object/speed, and a photoplethysmogram (PPG) sensor, that is, a sensor for detection of blood flow, pumped blood volume, and measurement of parameters of pulse wave propagation (pulse sensor), which allows the sensor to measure pulse, with the additional ability to suppress movement artifacts. Movement artifacts are measurement errors arising from the movement of an object (in the case of a PPG sensor, this is the addition of the signal from the movement of red blood cells and the signal from the displacement of the bracelet with the sensor relative to the hand; changes in the volume of blood vessels may also cause such errors).

FIG. 1 shows an embodiment of the multifunctional miniature sensor according to an embodiment of the disclosure.

Referring to FIG. 1, the miniature optical sensor comprises a radiation source 1; an optical circuit 3 including a collimating element 2 and two interconnected optical elements; receiver 10, wherein the radiation source 1 and the radiation receiver 10 are located in the same plane.

The optical circuit 3 includes a collimating element and two optical elements, a first optical element a and a second optical element b, connected to each other, wherein a connection surface of these optical elements is a common semitransparent surface 7, on which a parallel (collimated) radiation beam is to fall. The semitransparent surface 7 may be made in various known ways, for example, by applying a beam splitting coating to one of the surfaces to be connected.

The first optical element a comprises an input surface 4 configured for receiving radiation; and a reflective surface 5 of the first optical element configured to reflect radiation that has passed through the input surface 4, and direct the reflected radiation to the semitransparent surface 7.

A beam-splitting (semitransparent) coating is applied to the surface 7. The incident beam is split into two parts of the parallel radiation beam coming from the reflective surface 5 of the first optical element a into two parallel radiation beams, which are reference radiation and working radiation.

The first optical element a further includes a working surface 6 for emitting the working radiation reflected from the semitransparent surface 7 and receiving the radiation reflected from the object or scattered by the object.

The working surface 6 may be configured to focus the working radiation. Focusing occurs due to the refraction of light at the boundary of two media, the boundary of the media in this case being a surface of the optical element. The working surface 6 may be flat, spherical, aspherical, etc. The degree of focusing, that is, the curvature of the working surface 6, is determined by the type of object.

The second optical element b contains a reflective surface 8, and an exit surface 9.

Moreover, the reflective surface 8 of the second optical element b receives the reference radiation that has passed through the semitransparent surface 7. The radiation reflected/scattered by the object and the reference radiation are emitted from the output surface 9.

An interference pattern is formed on the plane of the radiation receiver 10, and the photodiode converts the radiation of the optical range incident thereon into a photocurrent.

Figure 2A:
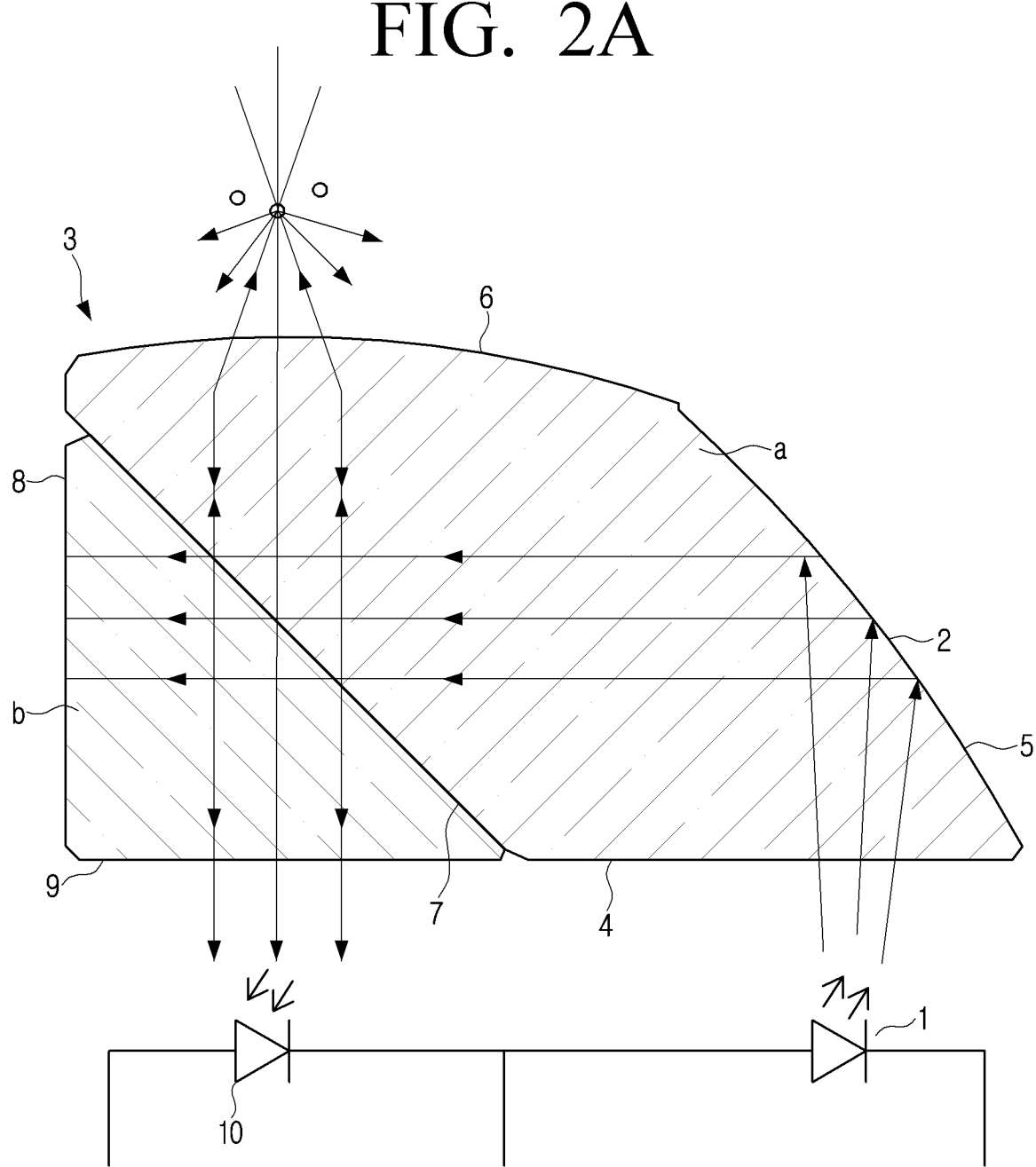
FIG. 2A shows an embodiment of the multifunctional miniature sensor, in which the reflective surface of the first optical element is made in the form of an off-axis parabolic mirror according to an embodiment of the disclosure.

FIG. 2A shows an embodiment of the disclosure, in which the collimating element is made in the form of an off-axis parabolic mirror. The production process of optical elements is such that an optical element is first produced with all the geometric features of surfaces, for example, surfaces in the form of an off-axis parabola, a sphere, an aspherical surface, etc. Appropriate coatings are then applied to the corresponding surfaces (e.g., beam-splitting, reflective, or antireflection coatings).

Figure 2B:
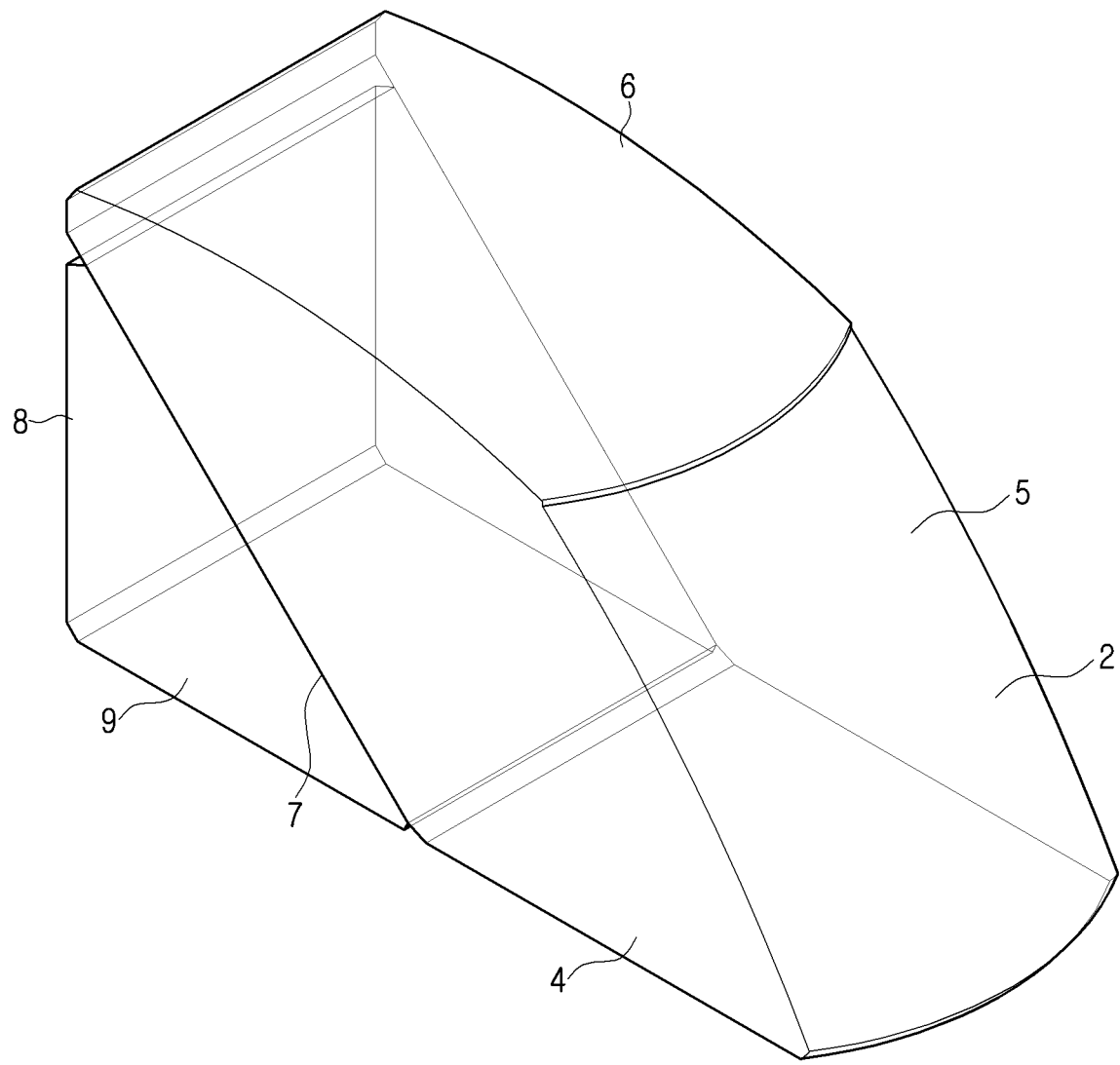
FIG. 2B is a three dimensional (3D) view of the embodiment of the inventive multi-functional miniature sensor shown in FIG. 2A according to an embodiment of the disclosure.

FIG. 2B is a three-dimensional (3D) view of the embodiment of the disclosure shown in FIG. 2A. Referring to FIG. 2B, the use of a free-standing collimating element in the form of a collimating lens is not required, since the diverging laser beam transmitted to the first optical element a of the optical circuit 3 is converted into a parallel beam due to the fact that the reflective surface 5 includes the collimating element 2 of the first optical element a, which is an off-axis parabolic mirror. In this case, during production of the sensor, the radiation source 1 is placed at the focus of the parabolic mirror for collimation.

For the radiation source 1 and the receiver 10 to be in the same plane, a part of the paraboloid is selected, where the collimated radiation is rotated by 90 degrees relative to the incident radiation. The characteristics of the parabolic mirror in this case are selected basing on the requirements for miniaturization of the geometric dimensions of the entire system. This configuration reduces the number of elements of a miniature sensor, that is, the design is simplified, and the overall dimensions and cost of the sensor are thereby reduced. In addition, the location of the radiation source and the radiation receiver in the same plane makes it possible to further reduce the dimensions of the sensor and simplify surface mounting of the sensor.

The collimating element for the first embodiment shown in FIG. 1 may be either a separate element or an element integrated with a laser diode or integrated into the first optical element a.

Figure 3A:
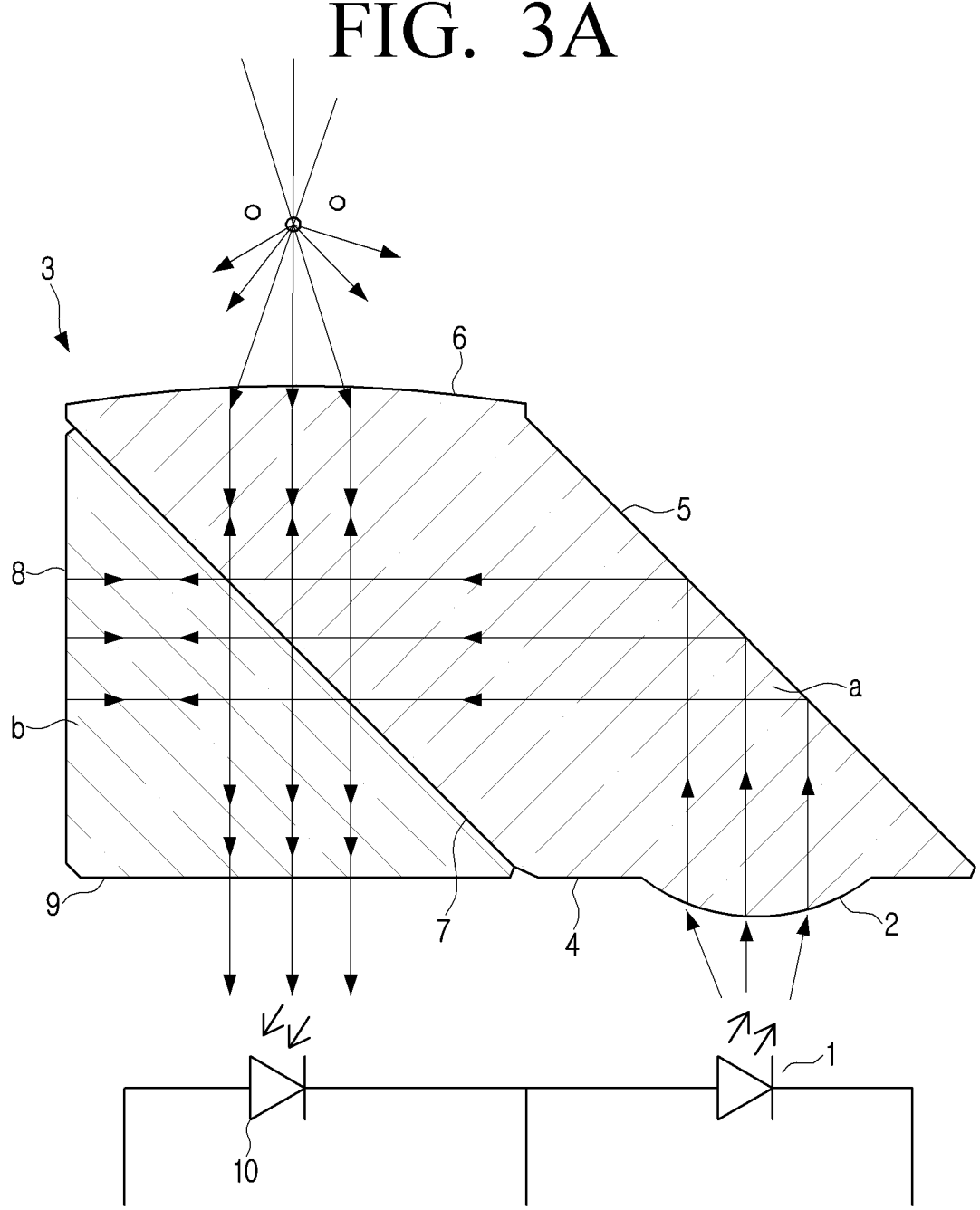
FIG. 3A shows schematically the multifunctional miniature sensor according to the invention, in which a collimating lens is integrated into an input surface of an optical circuit according to an embodiment of the disclosure.

FIG. 3A shows an embodiment of the disclosure in which the input surface 4 is made in the form of a collimating element according to an embodiment of the disclosure.

Figure 3B:
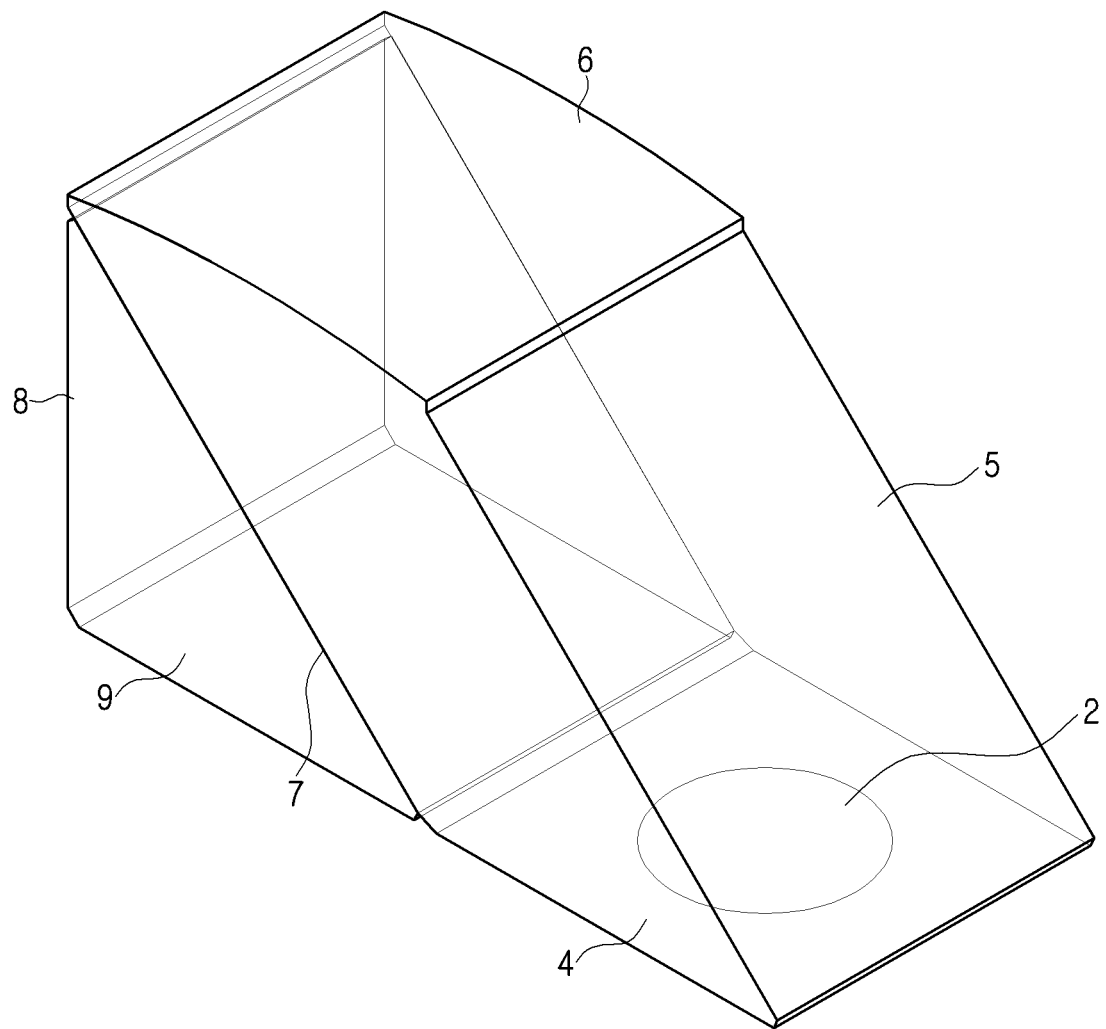
FIG. 3B is a 3D view of the embodiment of the inventive multi-functional miniature sensor shown in FIG. 3A according to an embodiment of the disclosure.

FIG. 3B is a 3D view of the embodiment of the disclosure shown in FIG. 3A according to an embodiment of the disclosure.

Figure 4A:
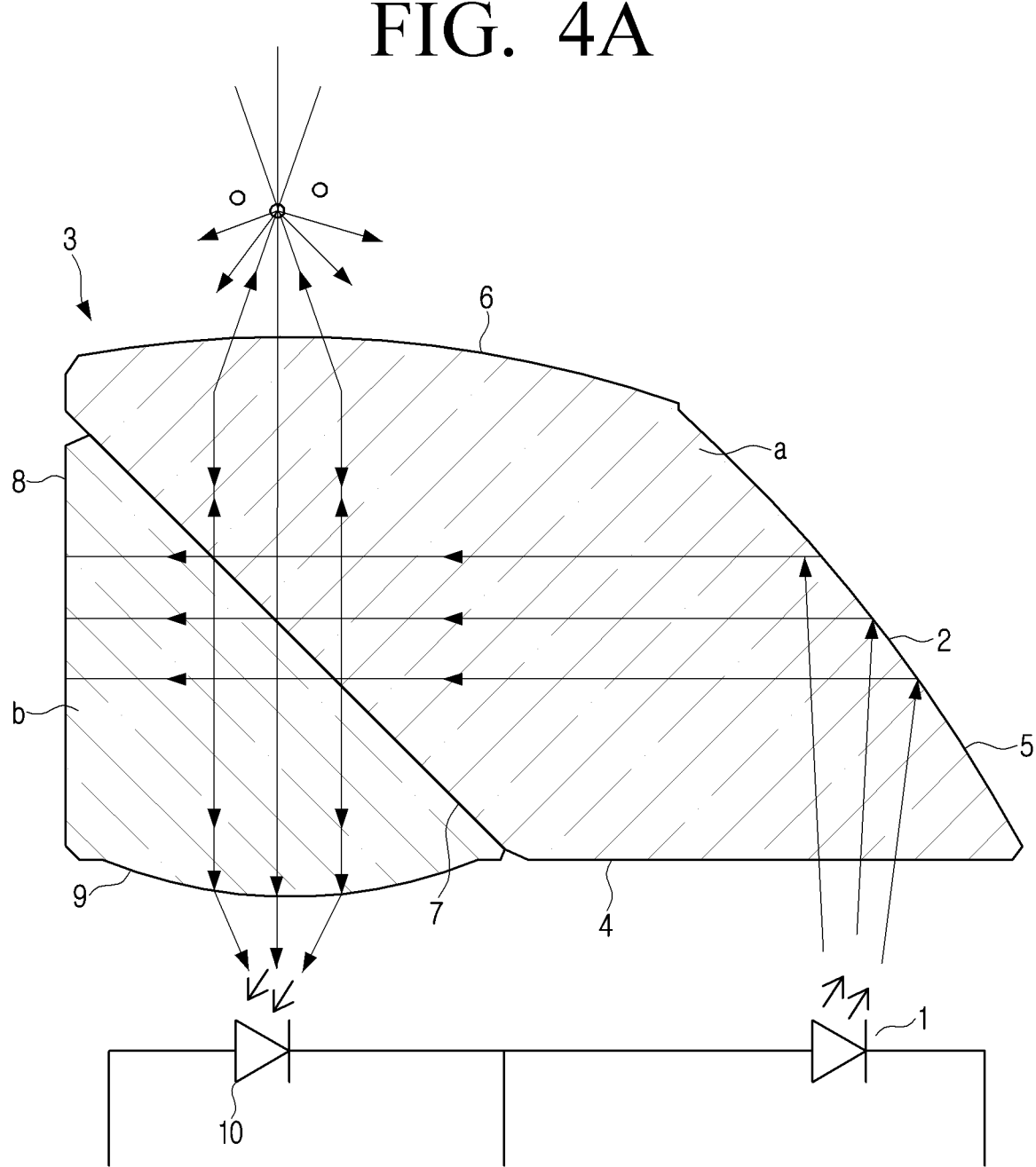
FIG. 4A illustrates an embodiment of the disclosure in which the output surface is configured to focus the emitted radiation according to an embodiment of the disclosure.

FIG. 4A shows an embodiment of the disclosure, in which the input surface 9 is configured to focus the emitted radiation, focusing occurs due to the refraction of light at the interface of two media, and the media interface is a surface of the optical element. The output surface 9 may have a curved shape. Focusing of the emitted radiation may be necessary for some type of photodetectors, for example, for high-speed photodetectors having small geometric dimensions, and may be used in any of the embodiments of the disclosure.

Figure 4B:
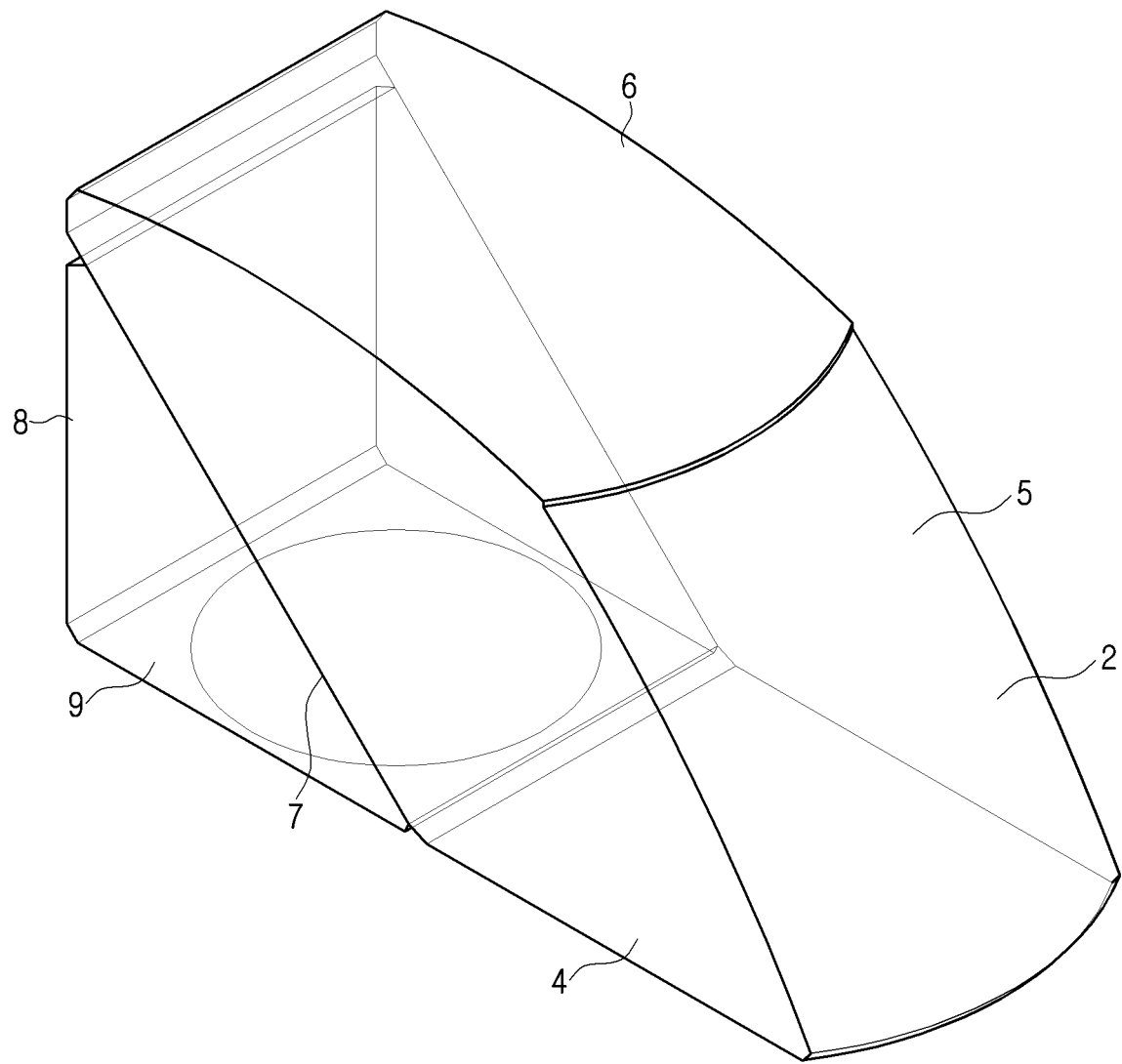
FIG. 4B is a 3D view of the embodiment of the disclosure shown in FIG. 4A according to an embodiment of the disclosure.

FIG. 4B is a 3D view of the embodiment of the disclosure shown in FIG. 4Aa according to an embodiment of the disclosure.

Figure 5A:
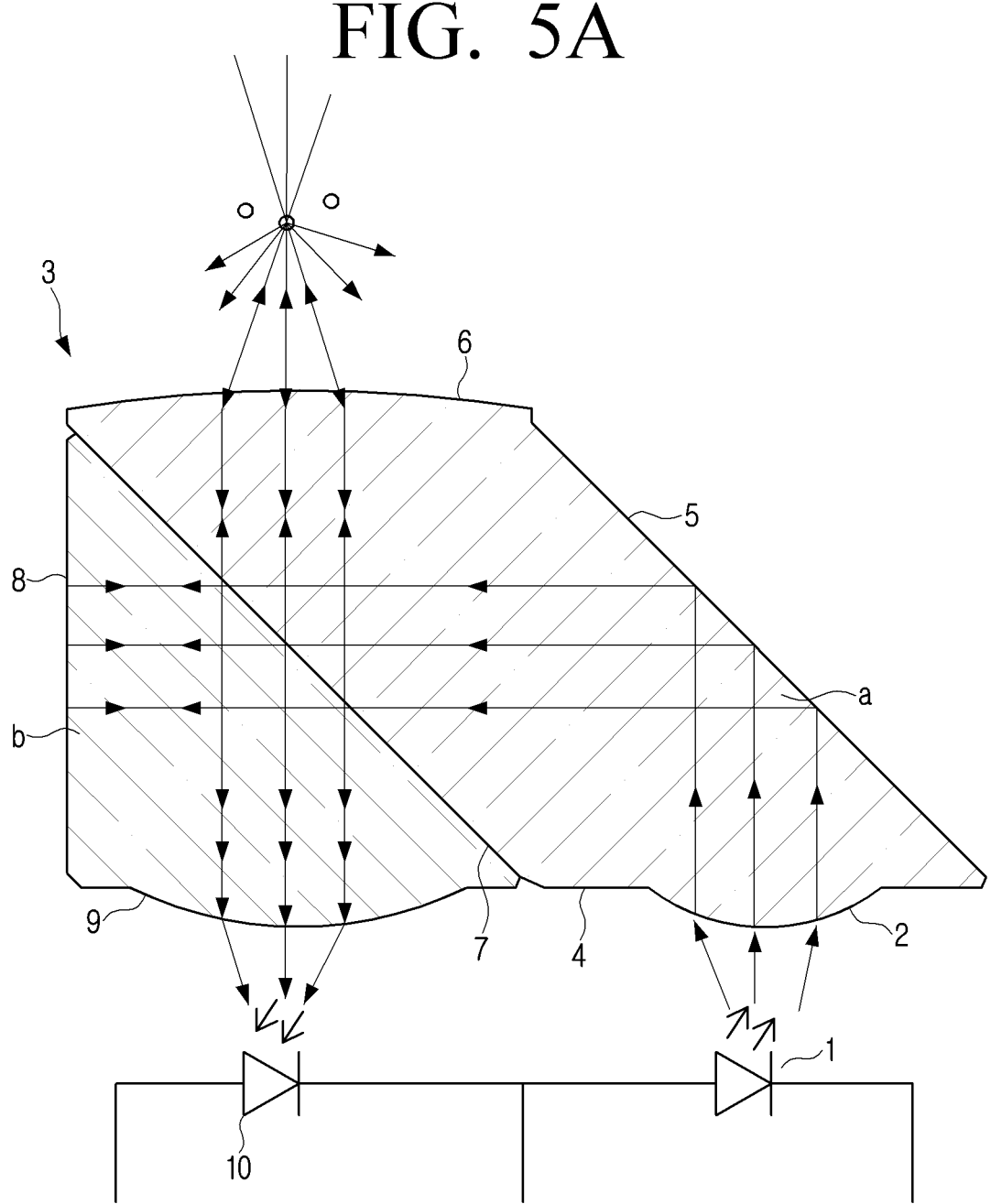
FIG. 5A shows an embodiment of the disclosure, in which the collimating lens is integrated into the input surface, and the output surface is configured to focus the emitted radiation according to an embodiment of the disclosure.
Figure 5B:
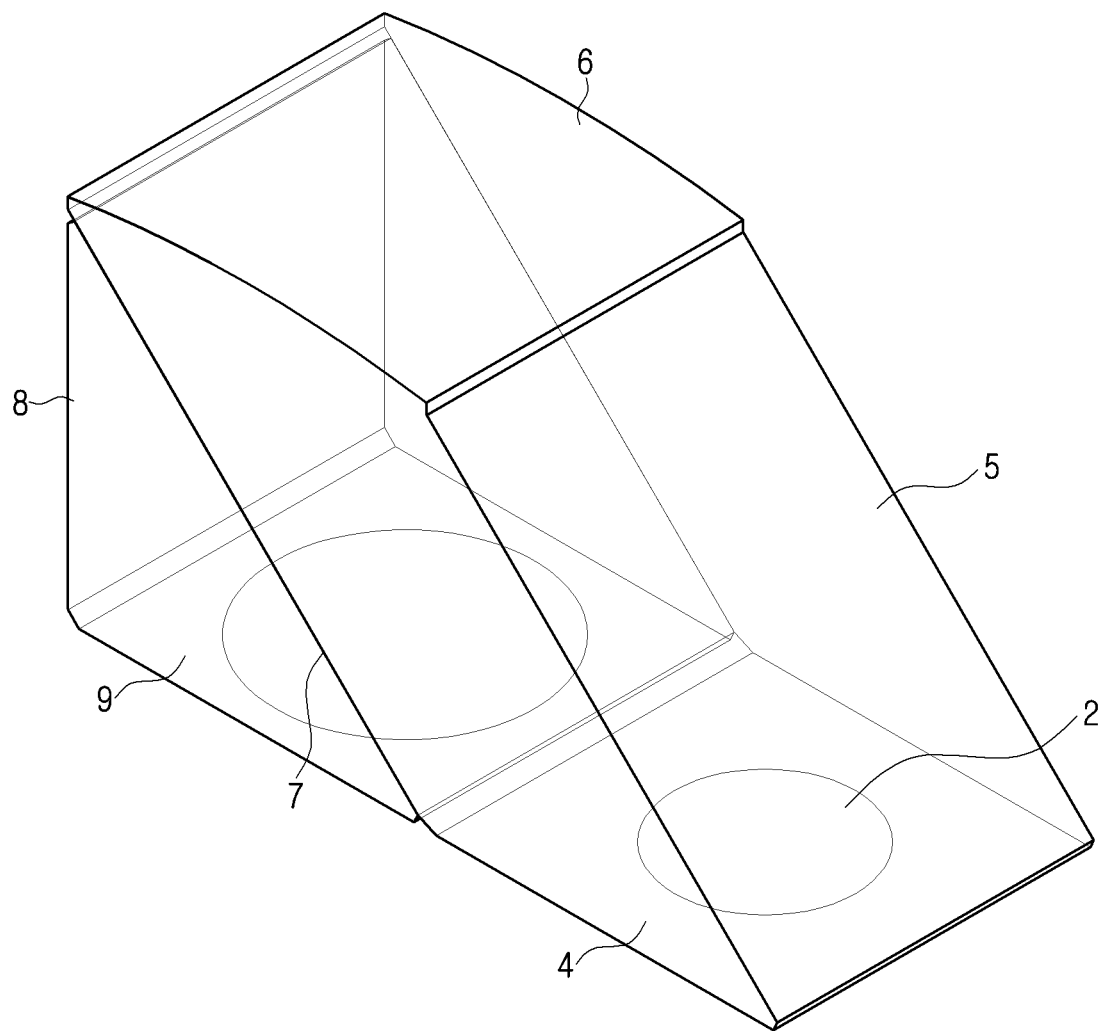
FIG. 5B is a 3D view of the embodiment of the disclosure shown in FIG. 5A according to an embodiment of the disclosure.

FIG. 5A illustrates an embodiment of the invention, in which the collimating element is integrated into the input surface 4 of the first optical element a of the optical circuit 3. The output surface 9 is made in the form of a curved surface configured to focus the emitted radiation, focusing occurs due to the refraction of light at the boundary of two media, the boundary media in this case is the output surface of the optical element. FIG. 5B is a 3D view of the embodiment of the disclosure shown in FIG. 5A.

Figure 6:
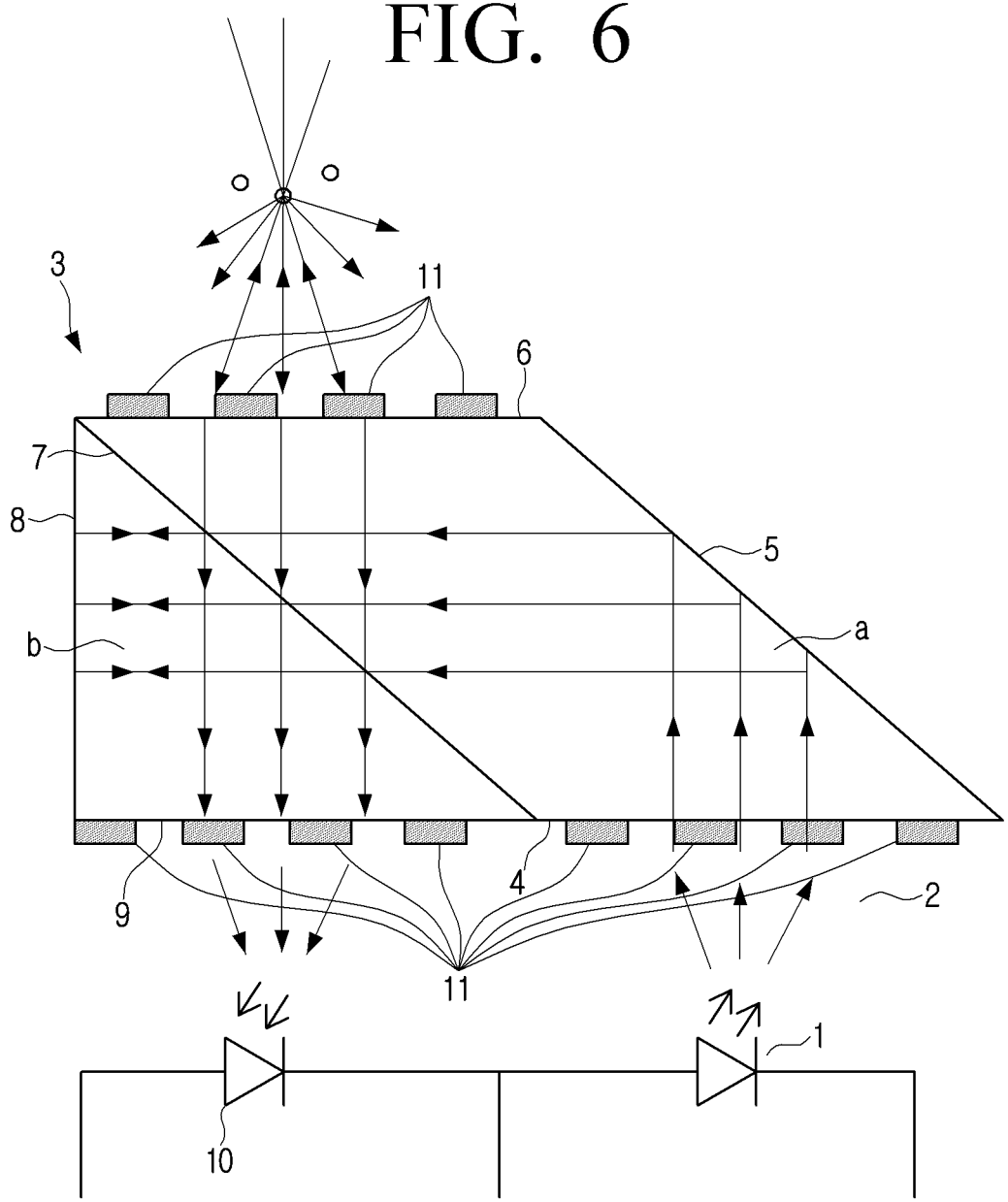
FIG. 6 illustrates an embodiment of the disclosure using diffraction gratings for focusing and collimation according to an embodiment of the disclosure.

FIG. 6 shows an embodiment of the disclosure, in which diffractive elements 11 are used to focus the working radiation, to focus the emitted radiation, to collimate the radiation (i.e., as a collimating element), such as, for example, widely used optical diffractive elements (DOE) or holographic diffractive elements (HOE) according to an embodiment of the disclosure.

Such diffractive elements may be applied to the surfaces of the first optical element a and the second optical element b and may be used to collimate and focus the transmitted radiation. It is possible to perform a combined version in which both lenses and diffraction gratings are used as focusing elements. The advantages of using DOE and/or HOE include that the geometry of the optical elements a and b becomes extremely simple; because all working surfaces in this case will be flat, a sensor with this configuration is the most compact. However, among the drawbacks, there are large losses of the optical signal on DOE and HOE elements in comparison with spherical and aspherical surfaces.

Referring to FIG. 6, the collimating element 2 may be applied in the form of DOE or HOE on the input surface 4 of the first optical element a, and the radiation from the radiation source 1 is collimated by means of the applied DOE or HOE.

Also FIG. 6 shows a DOE or an HOE applied to the working surface 6 of the first optical element a to focus the working radiation.

FIG. 6 also shows a DOE or an HOE applied to the output surface 9 of the second optical element b to focus the emitted radiation.

The use of DOEs or HOEs may further reduce the size of the sensor.

The radiation source 1 may be any suitable miniature emitting laser. It should be noted that a single mode vertical emitting laser (VCSEL) used as a radiation source has several advantages. The use of VCSELs, in comparison with conventional photodiodes, avoids mode hops, since such lasers are single-mode both longitudinally and transversely. In addition, the active radiation area of the VCSEL is symmetric, and represents an ideal circular beam which ensures good focusing. Further, VCSELs are inexpensive and resistant to unwanted optical feedback. The vertical radiation of the VCSELs simplifies mounting on the sensor. VCSELs may also be performed in an array, and thus can be used for multichannel applications.

Receiver 10 may be a photodiode, but may also be any suitable receiver such as a PIN photodiode, photomultiplier tube (PMT), avalanche photodiode, photoresistor, etc.

The working surface 6 may be a focusing surface and may be made in the form of a spherical lens or an aspherical lens, and may also be flat. The working surface is configured to focus the working radiation at a certain distance from the laser surface.

The optical circuit 3 is made monolithic due to rigid gluing of two optical elements. Such a monolithic structure includes all the necessary functions (beam direction, splitting, focusing), is well suited for surface mounting, is compact and reliable, because the optical circuit may not be misaligned when shaking, that is, for example, when the user actively uses a mobile device. In this case, surface mount refers to the installation (mounting) of the multifunctional miniature sensor directly on an electronic printed circuit board without the need to make holes from the side of conductive tracks (i.e., surface mount devices (smd) technology) using standard equipment together with other electronic components of the mobile device.

Since the radiation from the semitransparent surface 7 may partly return back to the radiation source through the input surface 4, this may lead to instability in the characteristics of the radiation emitted from the radiation source. To address this problem, a laser with a fixed polarization may be used as a radiation source 1, while a quarter-wave plate is built into the input surface of the first optical element. This design prevents back reflected radiation from entering the radiation source. A laser with a fixed polarization in combination with a quarter-wave plate acts as an optical isolator, because for a laser with a fixed polarization, radiation with the corresponding polarization, coinciding with the initial one, may return to the laser cavity, but the polarization of the radiation after passing twice the quarter-wave plate changes to orthogonal which may not return to the laser cavity.

In the following, embodiments of the disclosure will be considered, the design of which, in addition to the advantages mentioned above, avoids the loss of a part of the radiation that may return from the semitransparent surface 7 back to the radiation source through the input surface 4.

Figure 7A:
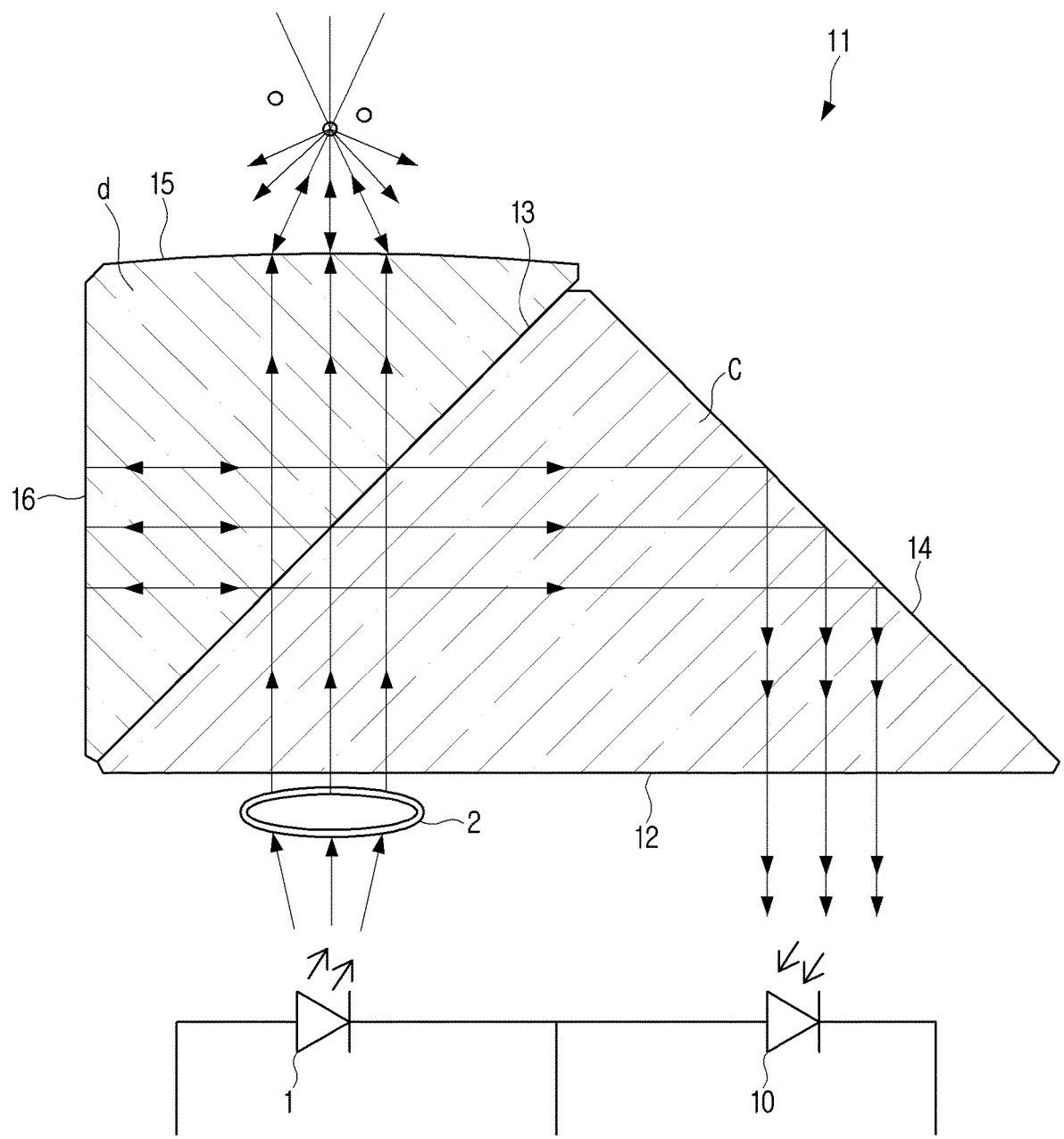
FIG. 7A illustrates an embodiment of a multi-channel dust sensor in which the receiver and the radiation source are located opposite to the input/output surface of the first optical element according to an embodiment of the disclosure.

Referring to FIG. 7A, the miniature sensor comprises a radiation source 1; an optical circuit 11 including a collimating element 2 and two optical elements c and d connected to each other; and a radiation receiver 10. The radiation source 1 and the radiation receiver 10 are located in the same plane.

The optical circuit 11 includes a collimating element 2 and two optical elements, a first optical element c and a second optical element d, connected to each other. The connection surface of these optical elements is a semitransparent surface 13 which divides the radiation from the radiation source 1, collimated by the collimating element 2 and passed inside the first optical element c through the input/output surface 12 of the first optical element c, into two beams (i.e., a reference beam and a working beam).

The reference beam is reflected from the semitransparent surface 13, hits the reflective surface 14 of the first optical element c, and after being reflected from the reflective surface 14, exits through the input/output surface 12 of the first optical element c, enters the receiver 10.

The working beam passes through the semitransparent surface 13, passes inside the second optical element d to the working surface 15, and is focused using the working surface 15. The focused working beam leaves the working surface 15, is reflected/scattered from the object, passes back to the second optical element d through the working surface 15, in the form of radiation reflected/scattered from the object, is reflected from the semitransparent surface 13, after being reflected passes to the reflective surface 16 of the second optical element d, is reflected from the reflective surface 16, after being incident again on the semitransparent surface 13 (taking into account only the path of the radiation useful for the sensor operation) passes through the semitransparent surface 13, after being incident on the reflective surface 14 of the first optical element c is reflected therefrom, couples the reference radiation, and leaves the input/output surface 12 of the first optical element c. An interference pattern is formed on the plane of the receiver 10, and the photodiode converts the incident radiation of the optical range into a photocurrent.

Figure 7B:
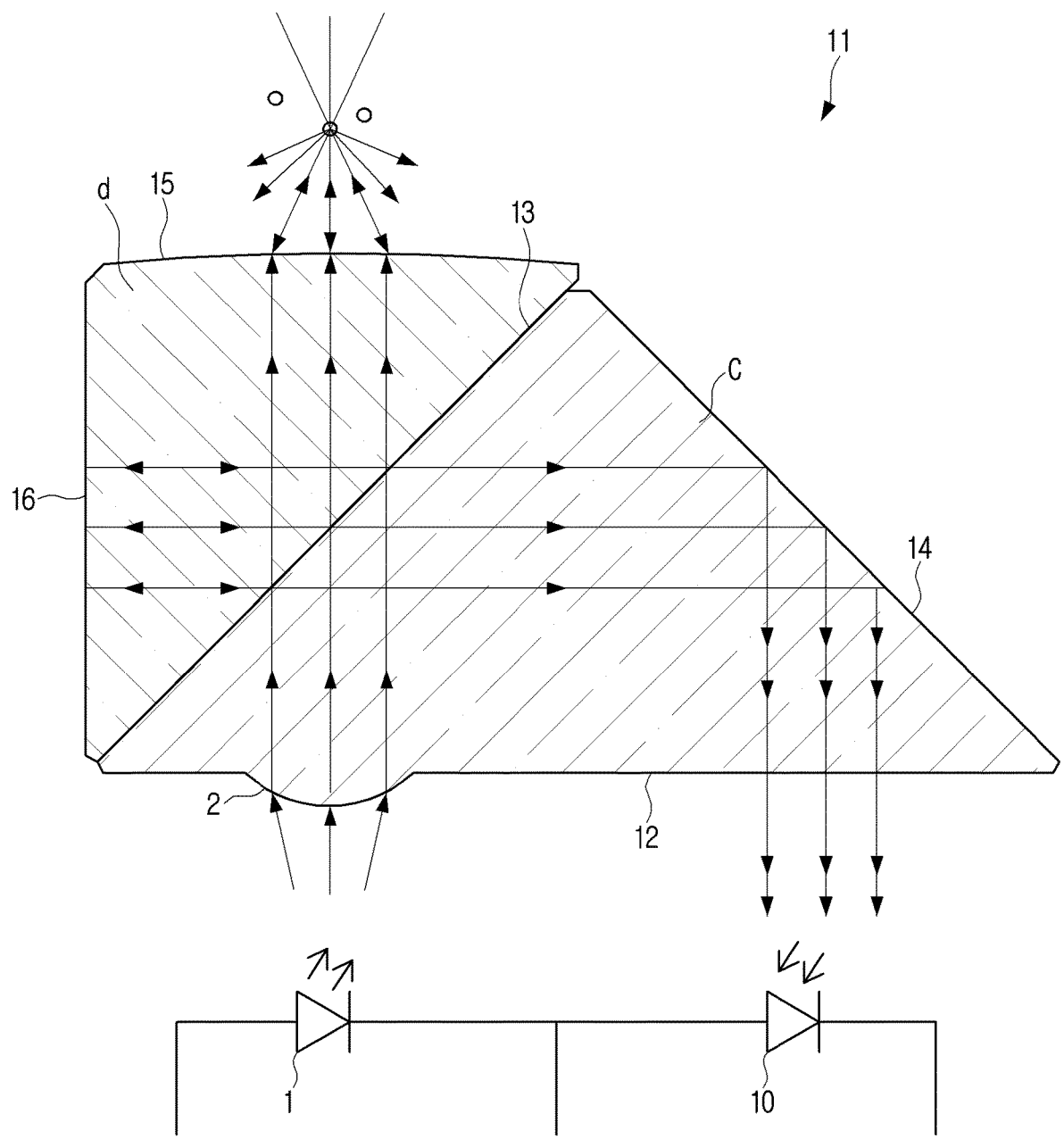
FIG. 7B shows schematically the miniature sensor, in which the collimating lens is integrated into the input surface of an optical circuit according to an embodiment of the disclosure.

FIG. 7B shows an embodiment of the disclosure, in which the part of the input/output surface 12, on which the radiation from the radiation source 1 is incident, is in the form of a collimating element 2, that is, the collimating element 2 is built into the input/output surface 12. This configuration reduces the number of elements, such that the overall dimensions and cost of the sensor are reduced.

Figure 7C:
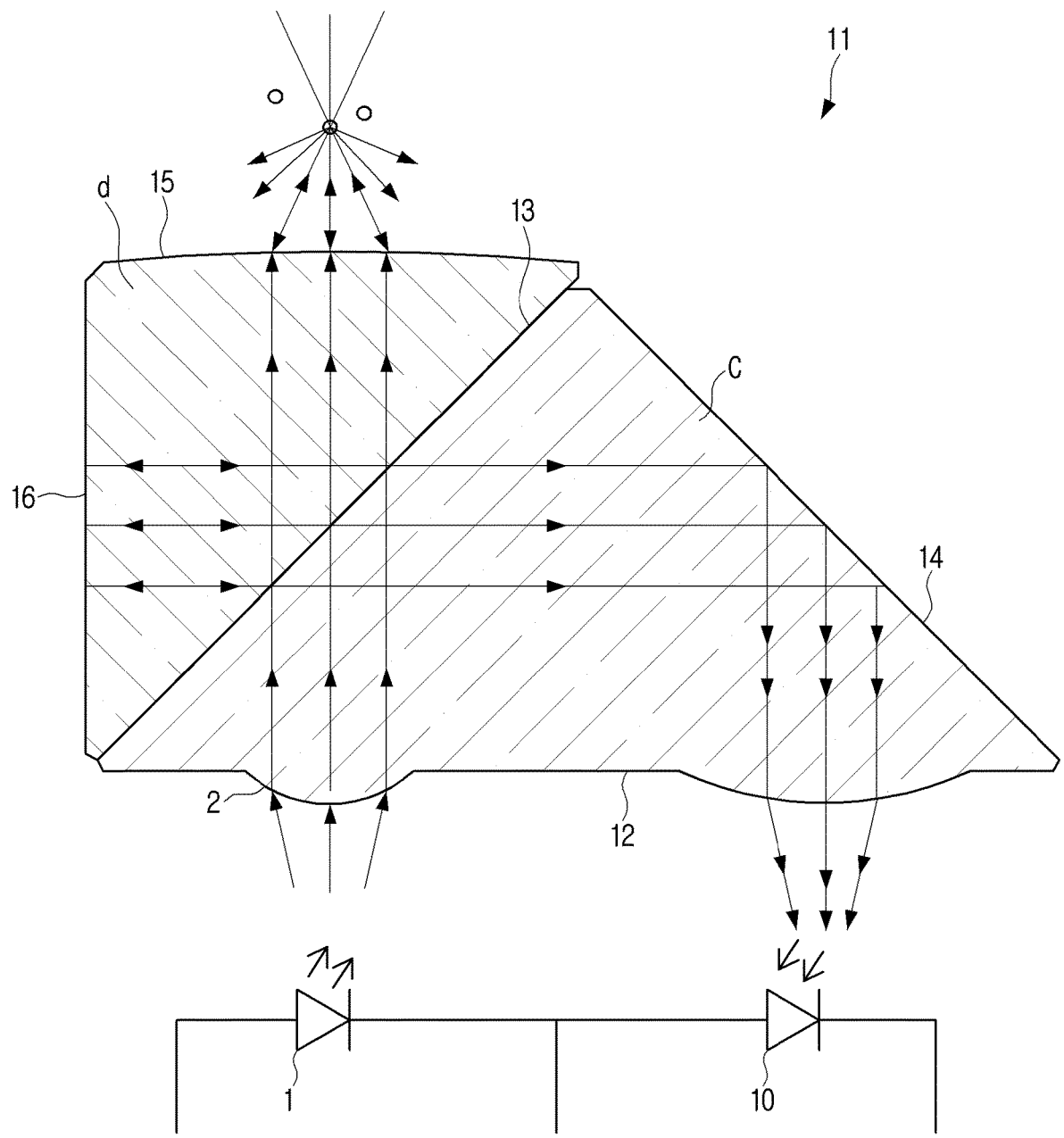
FIG. 7C illustrates an embodiment of the disclosure in which a collimating element is integrated into the input/output surface and the output surface is configured to focus the emitted radiation according to an embodiment of the disclosure.

FIG. 7C illustrates an embodiment of the disclosure, in which a collimating element 2 is integrated into the input/output surface 12, and the output surface 12 is also configured as a curved surface for focusing the emitted radiation.

Figure 8A:
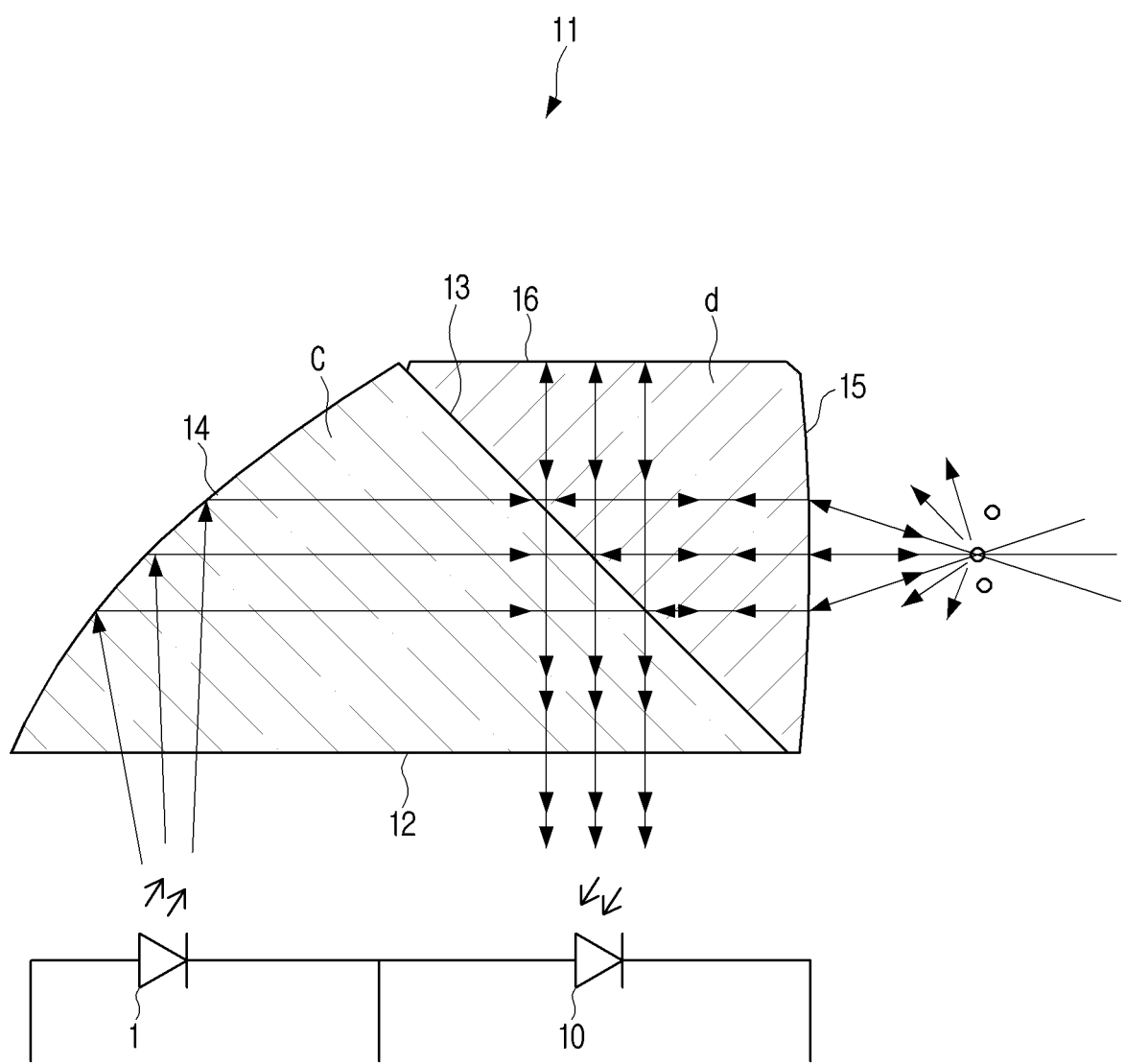
FIG. 8A illustrates an embodiment in which the receiver and the radiation source are located opposite to the input/output surface of the first optical element, and the reflective face of the first optical element is in the form of an off-axis parabolic mirror according to an embodiment of the disclosure.

FIG. 8A illustrates an embodiment of a multifunctional miniature sensor, in which the receiver and the radiation source are located opposite the input/output surface of the first optical element, and the reflective face of the first optical element is in the form of an off-axis parabolic mirror. This configuration reduces the number of elements of a miniature sensor, that is, simplifies the design, reduces the overall dimensions and the cost of the sensor.

The optical circuit 11 of FIG. 8A also includes a collimating element and two optical elements, a first optical element c and a second optical element d, connected to each other. The connection surface of optical elements c and d is a semitransparent surface 13.

Referring to FIG. 8A, the radiation from the radiation source 1 passes the input/output surface 12 and collimates, and after being reflected from the reflective surface 14 of the first optical element c, which is an off-axis parabolic mirror, is directed to the semitransparent surface 13, where it is divided into working radiation and reference radiation. The reference radiation is refracted by the semitransparent surface 13 and through the input/output surface 12 to the receiver 10. The working radiation is transmitted by the semitransparent surface 13, then enters the second optical element d and leaves the working surface 15. After being focused, the working radiation is scattered by the object, and the radiation scattered by the object through the working surface 15 re-enters the second optical element d, is reflected from the semitransparent surface 13, is directed to the reflective surface 16 of the second optical element d, enters the first optical element c through the semitransparent surface 13, and through the input/output surface 12 enters the receiver, which captures the interference pattern.

Figure 8B:
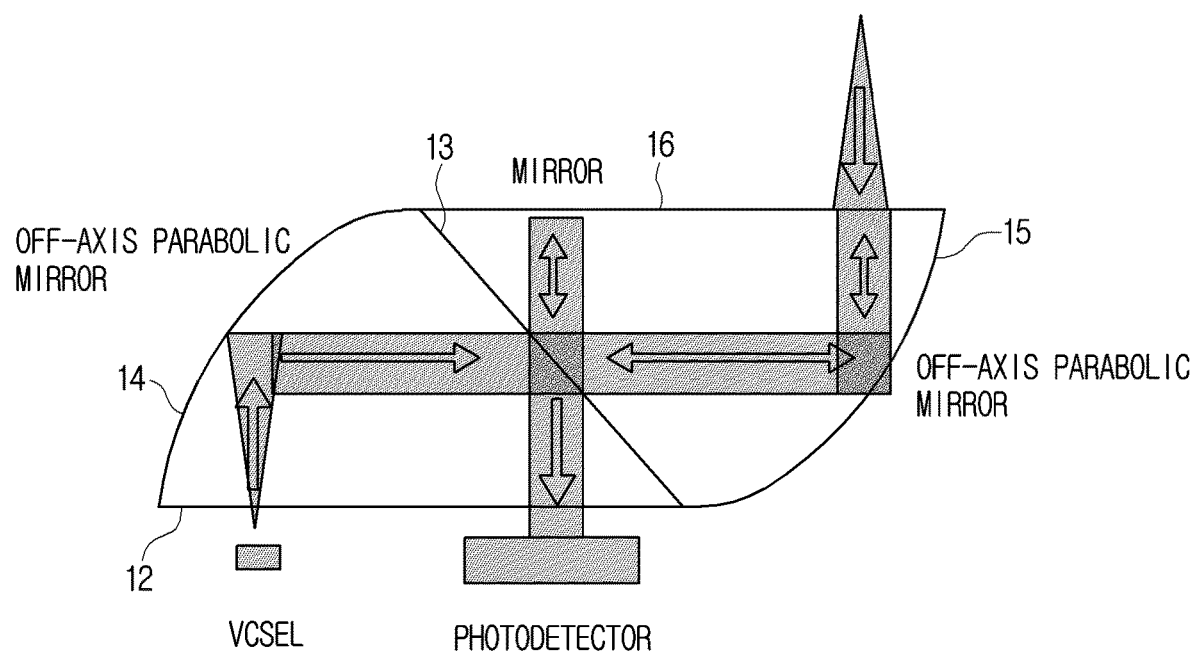
FIG. 8B illustrates an embodiment in which the optical circuit comprises two off-axis parabolic mirrors according to an embodiment of the disclosure.

Referring to FIG. 8B, the surface 15 may be in the form of an off-axis parabolic mirror. In this case, the surface 16 may be made in the form of a working surface on which the working radiation reflected from the surface 15 will be focused and directed towards the object. After being scattered by the object or reflected from the object, the radiation scattered by the object or reflected from the object will pass through the surface 16, will be reflected from the surface 15, will be reflected from the semitransparent surface 13, will fall again on the surface 16 where the mirror is located, after being reflected from the mirror, the radiation, scattered by the object or reflected from the object, will pass the semitransparent surface 13, and the interference pattern will be detected by the receiver (photodetector).

The area in which the working radiation may be focused is at a distance of 10-15 mm from the working surface of the miniature sensor, and the radiation power of the sensor is sufficient to detect micro-objects, namely, particles ranging in size from several microns to several millimeters, e.g., fine dust particles, blood cells when measuring blood flow, etc. The higher the radiation power, the larger the detection area is, which allows measurements to be made faster and more accurately; however, the sensor must be configured to be safe for the eyes, which limits the radiation power, so the output power is chosen close to the one allowed for a given wavelength.

Figure 10:
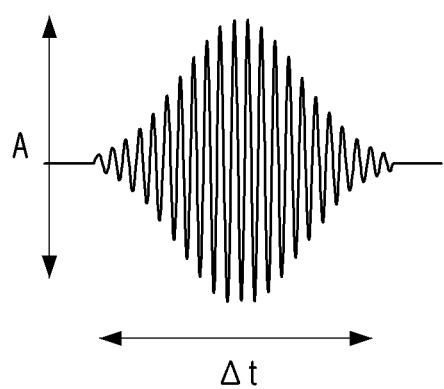
FIG. 10 illustrates the dependence of the variable component of the photocurrent, which contains a homodyne signal according to an embodiment of the disclosure.

It is possible to determine what was measured by the characteristic form of the signal. FIG. 10 shows a representative signal from single particles, and FIG. 11A shows a characteristic light detection and ranging (lidar) signal. When measuring the blood flow, that is, pulse, the sensor should be aimed at blood vessels (for example, at a finger or a wrist). In this case the probability of detecting dust particles is extremely low, and the user is aware of what kind of measurement is made.

The working radiation may also be scattered or reflected by macro-objects located at a distance of several meters from the working surface. To detect micro-objects and macro-objects, there are two different modes of operation, between which the sensor may be switched by the user.

When the sensor is operating in the mode of detecting micro-objects, the working radiation beam is not focused into a point, but the focusing area has an approximate estimated size of 5-10 microns and a focus length of 30-50 microns. Such an area, which is a space in which the working radiation is focused, will hereinafter be referred to as the "detection area." The detection area is an area of space where the density of the incident laser radiation is sufficient (usually calculated from the required signal-to-noise ratio) to detect the scattered radiation from the object having specified characteristics (size, material, etc.).

Micro-objects (dust particles, red blood cells, etc.) scatter very little light compared to macro-objects, so it is necessary to concentrate energy in a small area to detect micro-objects.

Figure 9:
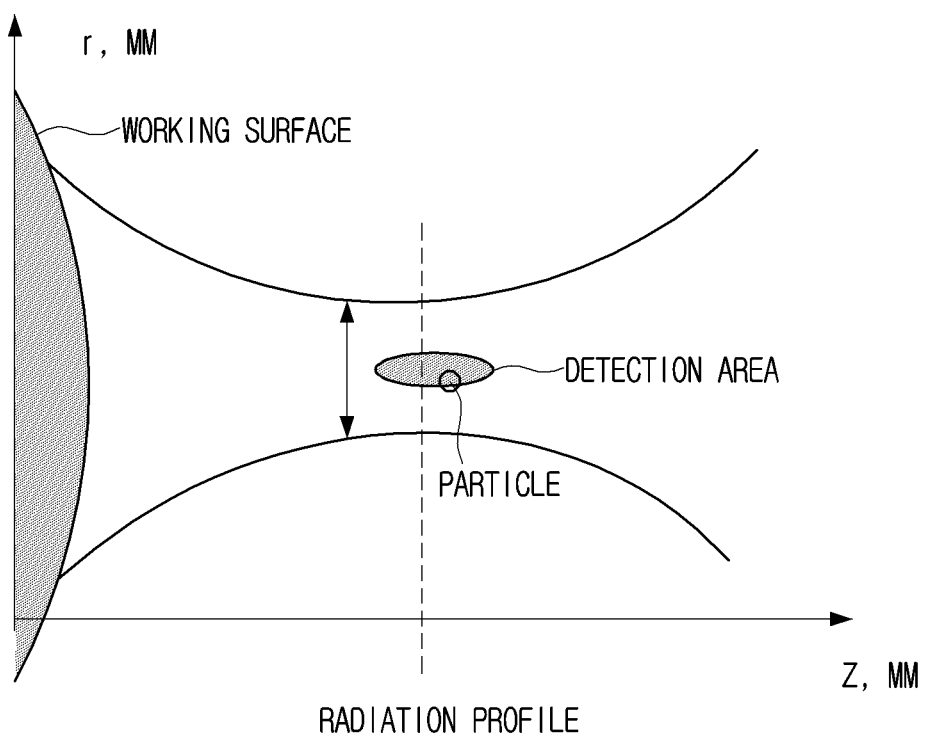
FIG. 9 illustrates the detection area that a micro-object enters according to an embodiment of the disclosure.

FIG. 9 shows the detection area in which a micro-object falls. The X-axis is the distance Z from the working surface, the Y-axis is the width r of the working surface, which focuses the working radiation according to an embodiment of the disclosure.

Referring to FIG. 9, the detection area is a space located near the 'waist', where the density of optical radiation is sufficient to detect a signal from an object. In this case, falling into the detection area, the micro-object is illuminated with a focused beam, that is, the intensity of the scattered radiation from the particle will be the highest in this particular space. The objects are illuminated with coherent radiation, and the scattered/reflected radiation from the object is optically mixed on a photodetector with reference radiation (homodyning).

FIG. 10 shows the relationship between the homodyne component of the photocurrent and time according to an embodiment of the disclosure. The graph shows the signals on the photodetector from a micro-object in the detection area. The backscattering of radiation by the micro-object depends on the particle size, i.e., large particles scatter more, and small particles scatter less. That is, by the amplitude (A) of the signal, one may judge the size of the particle. With the sensor, it is possible to determine the size of each micro-object in the detection area separately.

Equation 1 below is the formula for calculating the homodyne signal:

$$i_{hom} = 2\sqrt{i_{LO} i_{scat}} \cos(w_d t + \Delta\varphi(x,y,z)) \quad \text{Equation 1}$$

where $i_{hom}$ is a homodyne signal, which is the result of mixing the reference laser radiation and the scattered laser radiation on the sensitive area of the photodetector, and the component $i_{hom}$ room of the photocurrent is the result of mixing of two waves. In the case when the scattering object moves in a direction towards or away from the radiation source, this photocurrent contains the contribution of the Doppler effect ($W_d \neq 0$);

$i_{LO}$ is photocurrent corresponding to laser radiation of the reference beam;

$i_{scat}$ is photocurrent corresponding to laser radiation of the scattered beam;

$W_d$ is a Doppler frequency shift of laser radiation (i.e., the difference between frequencies of the reference radiation and radiation scattered by a moving object);

t is time;

$\Delta\varphi$ (x, y, z)$=\varphi_{LO}-\varphi_{scat}$ is a phase difference between oscillations of the reference and scattered beams;

$\varphi_{LO}$ is a phase of oscillation of laser radiation of the reference beam; and $\varphi_{scat}$ is a phase of oscillation of laser radiation of the scattered beam.

Equation 1 is used to determine $W_d$—Doppler frequency shift of the laser radiation.

The number of particles per unit volume is related to the concentration of particles as follows (particles are assumed to be spherical):

Nv is a number of particles per unit volume (1/m³);
is a particle density (kg/m³);
is a particle radius (m); and
C is a particle concentration (kg/m³).

Detection of individual particles with the measurement of their speed makes it possible to measure Nv:

$$N_v = \frac{N}{v \cdot t \cdot S} \quad \text{Equation 2}$$

where $N$ is a number of detected particles;
t is a measurement time (s);
S is an effective surface area of the detection area (m²) (the detection area is the area of the space in which the laser radiation is focused); and
v is a particle velocity (m/s), which is determined from the measurement of the Doppler frequency shift of the radiation.

Moreover, the particle velocity v is determined from Equation 3 as follows:

$$v = Wd * C / W_{LO} \quad \text{Equation 3}$$

where C is the speed of light, and $W_{LO}$ is the laser frequency.

Thus, having determined Wd from Equation 1, and the particle velocity from Equation 3, it is possible to determine the concentration of particles in a given detection area using Equation 2.

Homodyne reception (mode) is a kind of coherent reception based on mixing two electromagnetic waves (i.e., a reference wave and a signal wave). In contrast to heterodyne reception, both waves have one radiation source. As may be seen from Equation 1, the homodyne signal depends on the phase difference between the reference and scattered waves $\Delta\varphi$ (x, y, z); therefore, this method may be used for phase demodulation of the detected signal. The homodyne signal depends on the Doppler shift of the radiation frequency Wd, and this method is used to determine the particle velocity. The homodyne signal is also proportional to the amplitude of the reference radiation, which provides amplification of a small signal caused by the scattering of the micro-object.

If micro-objects fall not only in the detection area, then they will also scatter light, but with a lower intensity than in the detection area; that is, the contribution of radiation from such micro-objects may be neglected, due to its smallness, since most of the radiation energy is concentrated in the detection area.

In the case when the investigated medium is a collection of moving micro-objects, the problem of many-particle scattering arises, which contributes to the frequency structure of the photoelectric current and distorts the measurement results. For micro-objects moving with velocities on the order of 0.1 mm/s, the contribution of single events is the main one up to concentrations on the order of tens of mg/m³, which is an extremely large value. In general, while this error is unavoidable, the error appears at extremely high concentrations of micro-objects, at which the use of this sensor is impractical.

When mixing two waves, it is necessary to indicate on which element the mixing occurs. In order to detect the frequency shift, the reference beams and scattered beams must be focused in the plane of the receiver (photodetector).

With the sensor, the user may determine both dust concentration and the concentration of blood cells in the vessel. When a change in the concentration of blood cells (e.g., erythrocytes in a vessel) is determined, then the pulse is determined over time. During operation, the radiation of the red and near-infrared regions is used, while the user simply puts his finger to the working surface. In this case, the pulse is measured by the change in the concentration of blood cells, which is determined similarly to the concentration of dust.

The sensor may also operate as a high-sensitivity optical microphone. Such a microphone provides improved protection from interference. The sensor detects remotely vibrations of the user's facial muscles. Vibrations of the facial muscles simulate the distance to the sensor with the frequency of the voice, which leads to a corresponding simulation of the phase of the scattered wave relative to the reference wave. This causes a similar modulation in the detected signal.

The following describes the mode of operation of the sensor for detecting (examining) macro-objects located at a great distance from the working surface, that is, as a lidar. It should be noted that in the mode of detecting macro-objects and their speed, no radiation focusing is required, as this corresponds to the optimal mode of operation of the sensor as a lidar, since collimated radiation gives the maximum detection range of the macro-object. The sensor may operate as a lidar for the focused radiation, but the maximum distance at which an object may be detected will be shorter. The lidar will also operate, but at a shorter maximum distance; in this mode of operation, the functionality of the sensor is also preserved for detecting micro-objects near the focus.

In this mode, two modes of operation are possible: a laser wavelength tuning mode and a relative displacement measurement mode.

Laser wavelength tuning (scanning):

This embodiment uses a sweep along the laser wavelengths. This sweep may be realized by sweeping the pumping current of the laser. Backscattering of the radiation produces an oscillating signal at the detector. The frequency of the oscillating signals is linearly related to the distance to the macro object and the speed of the macro object relative to the sensor. Using the Fourier transform, one may simultaneously measure the distance to the macro object and the speed of the macro object.

A ramp voltage is applied to the radiation source 1, which is a laser, while the laser power also changes in a sawtooth. Due to the processes of heating the laser (the laser is heated up due to a change in the current, i.e., the higher the current, the higher the temperature), the radiation frequency (that is the wavelength as well) of the laser changes. When the laser is heated, the radiation frequency shifts to the long-wave region. When reflected from a macro-object, such radiation will have oscillations, and the frequency of the oscillations of the radiation reflected from the macro-object is proportional to the distance to the macro-object.

Figure 11B:
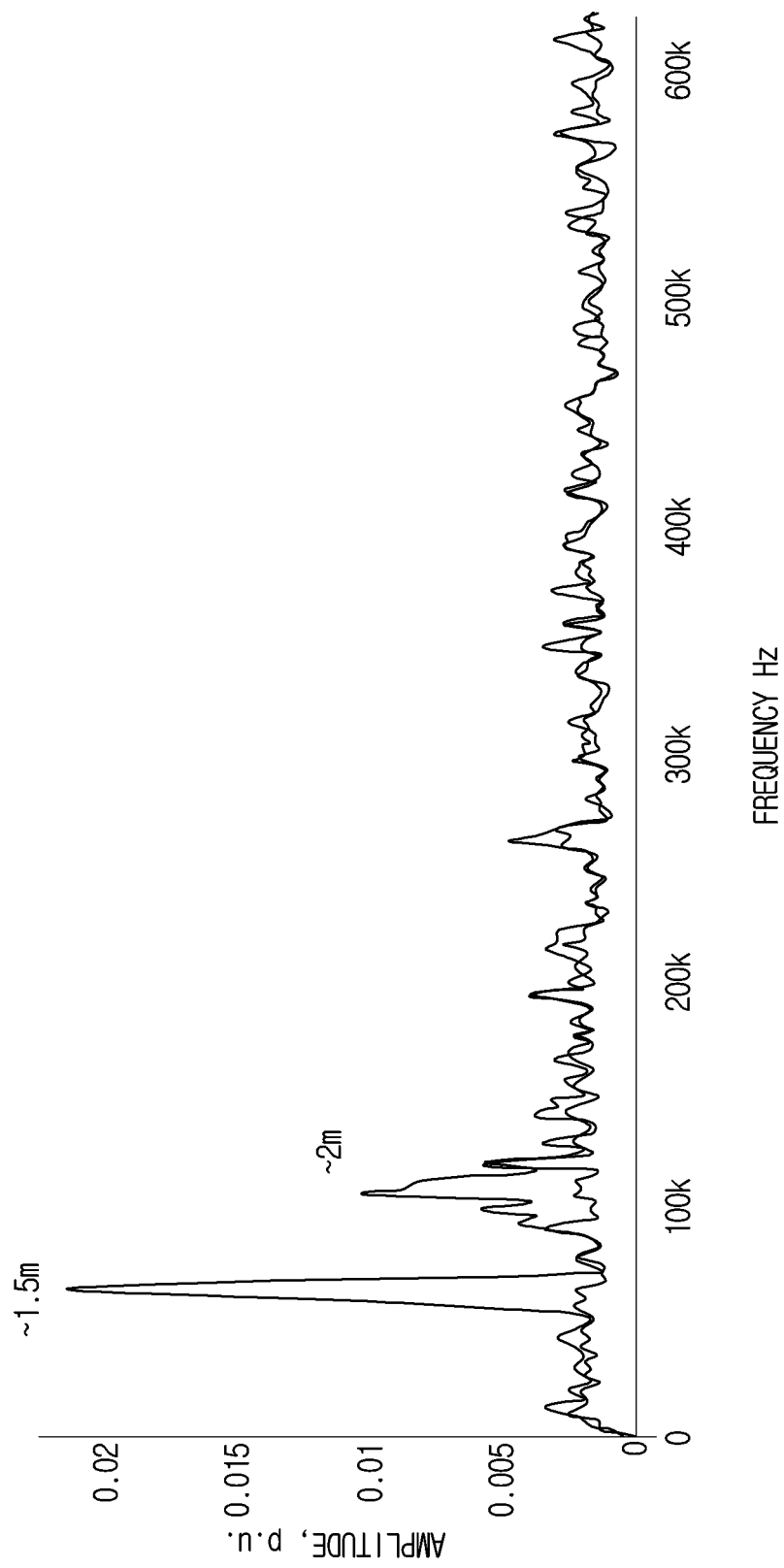
FIG. 11B is a graph of amplitude of the signal reflected from the macro object versus frequency according to an embodiment of the disclosure.

FIG. 11A illustrates a graph of the voltage of the signal reflected from the macro object versus time according to an embodiment of the disclosure. After the Fourier transform of this dependence, a graph of the amplitude of the signal reflected from the macro-object versus the frequency is obtained, shown in FIG. 11B, the results are obtained for a stationary object according to an embodiment of the disclosure. In the presence of modulation of the frequency (radiation wavelength) of laser radiation, the phase of the reflected signal changes in accordance with the change in the wavelength. At each moment of time, at a distance to the object, a different number of wavelengths fit, which leads to oscillations in the detected signal. Because the sensor uses phase-sensitive reception, this principle is analogous to a frequency-modulated continuous-wave (FMCW) lidar method. Equation 4, below, is the formula for calculating the position of the peak in the spectrum from which the distance to the object may be calculated:

$$f = 2L\Delta v/\Delta T \qquad \text{Equation 4}$$

where $\Delta T$ is the modulation pulse width [s];

$\Delta v$ is the range of variation of the frequency of laser radiation in wave numbers [1/cm], wave number $v=1/\lambda$, where $\lambda$ is the wavelength of laser radiation;

L is the distance to the object [cm]; and f is the position of the peak in the spectrum [Hz].

Relative displacement measurement mode:

In this mode, it is possible to determine the displacement of the object relative to an initial position, i.e., the initial position is taken as 0, and the instantaneous velocity of the object is calculated. Determining the speed of a macro object corresponds to determining the speed of the micro object. Since the speed and time of movement of the macro object are known, the change in the position of the macro object relative to the initial position may be determined.

Figure 12:
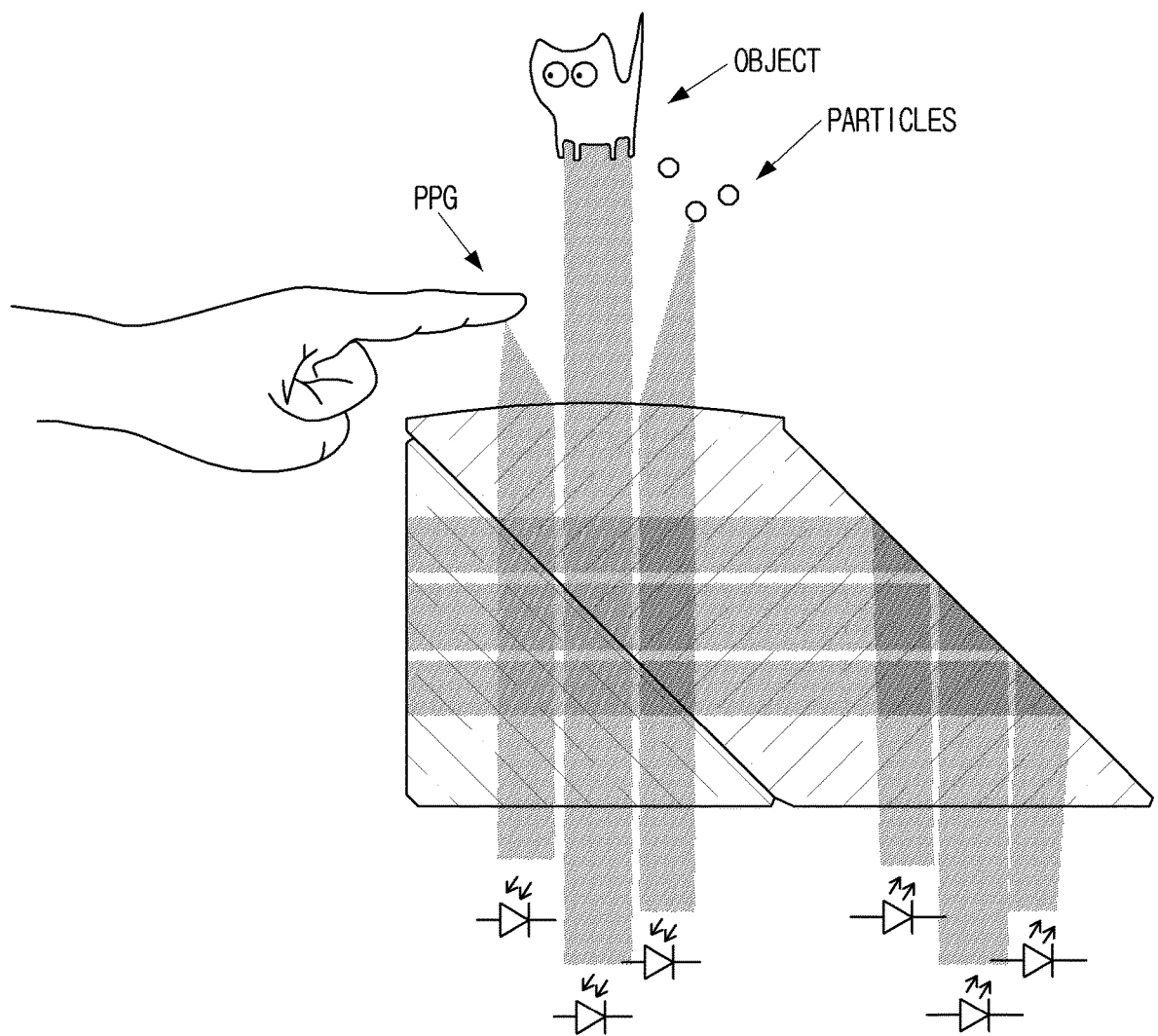
FIG. 12 illustrates a miniature sensor comprising a plurality of measurement channels performing various functions simultaneously according to an embodiment of the disclosure.

FIG. 12 shows a multifunctional miniature sensor containing a plurality of measurement channels performing different functions simultaneously according to an embodiment of the disclosure.

The miniature sensor may provide not only one measuring channel with a radiation source and a radiation receiver, but a plurality of measuring channels, each of which will have its own separate radiation source and a corresponding radiation receiver. Each measuring channel from a plurality of measuring channels may perform its function; for example, one of the channels may measure the pulse, another channel may detect the speed of distant objects and the distance thereto, and another channel may measure the dust concentration. The radiation source of each measuring channel has an appropriate wavelength.

Each measuring channel may be provided with its own required focal length, determined by the type of an object under study. For example, a short focal length is used for a PPG sensor, a medium focal length is used for dust, and a long focal length is used for a distance sensor. The focal length of one measuring channel may be made variable by increasing the complexity of the system, for example, using an adaptive lens or adding a moving element.

Due to its compact size, the miniature sensor may be built into a regular smartphone, and may also be used in devices such as smart watches, as well as in household appliances, for example, in robotic vacuum cleaners, which require the detection of micro-objects and macro-objects, air conditioners, etc. As described, one miniature sensor may have many functions: detecting the dust concentration, detecting the user's pulse, detecting the distance to an object and the speed of the object, and using it as a highly sensitive microphone.

The sensor may be used for games and applications that use a combination of virtual reality and actual reality to compensate for rendering errors caused by the user's movement relative to a scene. The sensor may accurately detect displacement, speed relative to the scene, and distance to real world objects. This information may be used as a feedback signal to improve the comparison of virtual reality objects with real world objects. Information about the user's movement may be included in various scenarios of user interaction with virtual reality objects.

The miniature sensor may also be used as an inexpensive analogue of time-of-flight (TOF) sensors.

While the disclosure has been described with reference to some illustrative embodiments, it should be understood that the essence of the disclosure is not limited to these specific embodiments. On the contrary, the essence of the disclosure is intended to include all alternatives, corrections, and equivalents that may be included within the spirit and scope of the claims.

In addition, the disclosure retains all equivalents of the claims even if the claims are amended in the course of consideration.

According to an embodiment, the various embodiments as described above may be implemented with software including instructions stored in the machine-readable storage medium readable by a machine (e.g., a computer). The apparatus may be an apparatus which may call instructions from the storage medium and operates according to the called instructions, and may include an electronic apparatus (e.g., electronic apparatus (A)) in accordance with the disclosed embodiments. When an instruction is executed by a processor, the processor may perform functions corresponding to the instruction, either directly or under the control of the processor, using other components. The instructions may include a code made by a compiler or a code executable by an interpreter. A machine-readable storage medium may be provided in the form of a non-transitory storage medium. A "non-transitory" storage medium may be a storage medium that does not include a transitory signal and is tangible, but does not distinguish between whether data is stored semi-permanently or temporarily on the storage medium.

According to an embodiment, the method according to various embodiments disclosed herein may be provided in a computer program product. A computer program product may be exchanged between a seller and a purchaser as a commodity. A computer program product may be distributed in the form of a machine-readable storage medium (e.g., compact disc read only memory (CD-ROM)) or distributed online through an application store (e.g. PlayStore™). In the case of on-line distribution, at least a portion of the computer program product may be stored temporarily or at least temporarily in a storage medium such as a manufacturer's server, a server of an application store, or a memory of a relay server.

Each of the elements (for example, a module or a program) according to various embodiments may be composed of a single entity or a plurality of entities, and some sub-elements of the abovementioned elements may be omitted. The elements may be further included in various embodiments. Alternatively or additionally, some elements (e.g., modules or programs) may be integrated into one entity to perform the same or similar functions performed by each respective element prior to integration. Operations performed by a module, program, or other element, in accordance with various embodiments, may be performed sequentially, in a parallel, repetitive, or heuristically manner, or at least some operations may be performed in a different order.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An optical sensor, comprising:
    at least one pair comprising a radiation source and a corresponding radiation receiver; and
    an optical circuit including a collimating element, a first optical element, and a second optical element,
    wherein the collimating element is configured to collimate radiation from the radiation source,
    wherein the first optical element and the second optical element are interconnected by a common surface,
    wherein the first optical element comprises:
        an input surface for receiving radiation,
        a reflective surface for reflecting radiation that has passed through the input surface and directing the reflected radiation to the common surface, and
        a working surface for emitting the radiation reflected from the common surface and receiving radiation reflected from an object or scattered by an object,
    wherein the second optical element comprises:
        a reflective surface for reflecting the radiation that has passed through the common surface, and
        an output surface for emitting the radiation that has passed through the common surface and the radiation reflected from the object or scattered by the object to the radiation receiver corresponding to the radiation source,
    wherein all radiation sources and radiation receivers are located in a same plane,
    wherein a quarter-wave plate embedded in the input surface of the first optical element, and
    wherein the radiation source comprises a laser with a fixed polarization.

2. The optical sensor of claim 1,
    wherein the common surface is configured to separate radiation from the reflective surface of the first optical element into reference radiation and working radiation,
    wherein the working surface of the first optical element is configured to emit the working radiation reflected from the common surface,
    wherein the output surface of the second optical element is configured to reflect the reference radiation that has passed through the common surface,
    so as to emit the reference radiation to the radiation receiver corresponding to the radiation source.

3. The optical sensor of claim 1, wherein the collimating element is integrated with the radiation source.

4. The optical sensor of claim 1, wherein the collimating element is integrated with the first optical element.

5. The optical sensor of claim 4, wherein the collimating element is integrated with the reflective surface of the first optical element, and is in a form of an off-axis parabolic mirror.

6. The optical sensor of claim 1, wherein the working surface is configured to focus the working radiation.

7. The optical sensor of claim 6, wherein the working surface is coated with a diffractive optical element (DOE) or a holographic optical element (HOE).

8. The optical sensor of claim 6, wherein the working surface is in a form of a spherical lens or an aspherical lens.

9. The optical sensor of claim 1, wherein the working surface is flat.

10. The optical sensor of claim 1, wherein the radiation source comprises a vertical emitting laser (VCSEL).

11. The optical sensor of claim 1, wherein the output surface is configured to focus the emitted radiation.

12. The optical sensor of claim 1, wherein the collimating element is in a form of a diffractive optical element (DOE) or a holographic optical element (HOE).

13. The optical sensor of claim 1, wherein the collimating element is in a form of a diffractive optical element (DOE) or a holographic optical element (HOE) applied to the input surface of the first optical element.

14. The optical sensor of claim 1, wherein the optical sensor is configured to function as at least one of a microphone, a dust sensor, a lidar, or a photoplethysmogram (PPG) sensor.

15. The optical sensor of claim 1, wherein the common surface is planar.

16. The optical sensor of claim 1, wherein the common surface forms a 45-degree angle with input surface and the output surface.

17. The optical sensor of claim 1, wherein the input surface and the output surface are in a second same plane.

18. An optical sensor, comprising:
    at least one pair comprising a radiation source and a corresponding radiation receiver; and
    an optical circuit including a collimating element, a first optical element, and a second optical element,
    wherein the collimating element is configured to collimate radiation from the radiation source,
    wherein the first optical element and the second optical element are interconnected by a common surface, the common surface being a semitransparent surface, wherein the first optical element comprises:
an input/output surface for:
inputting radiation from the radiation source and directing to the semitransparent surface, wherein the semitransparent surface is configured to divide the radiation input through the input/output surface into reference radiation and working radiation, and
emitting the reference radiation and the radiation reflected from an object or scattered by the object to the radiation receiver, and
a reflective surface of the first optical element for directing the reference radiation reflected from the semitransparent surface and the radiation reflected from the object or scattered by the object to the input/output surface for emitting from the optical circuit to the radiation receiver,
wherein the second optical element comprises:
a working surface for emitting the working radiation that has passed through the semitransparent surface and receiving the radiation reflected from the object or scattered by the object, and
a reflective surface for directing radiation reflected from the object or scattered by the object through the semitransparent surface to the reflective surface of the first optical element,
wherein all radiation sources and radiation receivers are located in a same plane,
wherein a quarter-wave plate embedded in the input surface of the first optical element, and
wherein the radiation source comprises a laser with a fixed polarization.

19. The optical sensor of claim 18, wherein the collimating element is integrated with the radiation source or integrated with the first optical element.

20. The optical sensor of claim 18,
wherein the input-output surface is configured to focus the emitted radiation,
wherein the working surface is configured to focus the working radiation, and
wherein the working surface is in a form of a spherical lens or an aspherical lens.

21. The optical sensor of claim 18,
wherein the working surface is coated with a diffractive optical element (DOE) or a holographic optical element (HOE), and
wherein the collimating element is in the form of a DOE or an HOE, or in the form of the DOE or the HOE applied to the input-output surface of the first optical element.

22. The optical sensor of claim 18, wherein the optical sensor is used as at least one of a microphone, a dust sensor, a lidar, or a photoplethysmogram (PPG) sensor.

* * * * *